United States Patent
Stewart et al.

(10) Patent No.: US 8,426,207 B2
(45) Date of Patent: Apr. 23, 2013

(54) METHODS, SYSTEMS AND DEVICES FOR ANALYZING A BIOLOGICAL FLUID SAMPLE FOLLOWING ION EXCHANGE

(75) Inventors: Ray F. Stewart, Belmont, CA (US); Aaron Dickerman-Stewart, Redwood City, CA (US)

(73) Assignee: Cantimer, Inc., Menlo Park, CA (US)

( * ) Notice: Subject to any disclaimer, the term of this patent is extended or adjusted under 35 U.S.C. 154(b) by 84 days.

(21) Appl. No.: 12/736,889

(22) PCT Filed: May 20, 2009

(86) PCT No.: PCT/US2009/003146
§ 371 (c)(1), (2), (4) Date: Nov. 19, 2010

(87) PCT Pub. No.: WO2009/142742
PCT Pub. Date: Nov. 26, 2009

(65) Prior Publication Data
US 2011/0076776 A1    Mar. 31, 2011

Related U.S. Application Data

(60) Provisional application No. 61/128,280, filed on May 20, 2008.

(51) Int. Cl.
*G01N 33/487* (2006.01)
*G01N 33/48* (2006.01)
*G01N 33/50* (2006.01)
*B01J 19/00* (2006.01)

(52) U.S. Cl.
USPC ............. 436/2; 436/63; 436/74; 436/148; 436/149; 436/151; 436/164; 436/95; 436/98; 436/108; 436/86

(58) Field of Classification Search ........... 436/2, 63, 436/71, 73, 74, 148, 149, 151, 161, 164, 436/95, 98, 106, 108, 129, 86, 133, 182, 177, 178; 422/68.1, 82.01, 82.02, 82.13, 422/69
See application file for complete search history.

(56) References Cited

U.S. PATENT DOCUMENTS

| 5,409,737 | A  | * | 4/1995  | Kozak et al. ............ 427/435 |
| 6,265,224 | B1 | * | 7/2001  | Collis et al. ............ 436/178 |
| 7,063,980 | B2 | * | 6/2006  | Tachino ................... 436/17 |
| 2005/0164299 | A1 |   | 7/2005  | Stewart |
| 2007/0161124 | A1 | * | 7/2007  | Schuchard et al. ........ 436/518 |
| 2007/0249059 | A1 |   | 10/2007 | Stewart |

FOREIGN PATENT DOCUMENTS

| DE | 10028837 A1 | 12/2001 |
| EP | 1396726 A   | 3/2004 |
| JP | 2005-265858 | 9/2005 |
| WO | WO 2005/003821 A2 | 1/2005 |
| WO | WO 2005/124344 A  | 12/2005 |

OTHER PUBLICATIONS

International Search Report from related PCT Patent Application No. PCT/US2009/003146 mailed on Oct. 16, 2009, now published as WO 2009/142742 A1 on Nov. 26, 2009.
Labmate Online, "New chrornaband HR-X from Macharey-Nagel", Apr. 8, 2008 Online Article, 1 page, Retreived from the Internet on Aug. 11, 2009 from URL:http://www.labmate-online.com/news/chromatography-and-specroscopy/1/machery-nagel-gmbh/new-chromabond-hr-x-from-machery-nagel/1303/> Abstract.
Stewart, et al., "Human hydration level monitoring using embedded piezoresistive microcantilever sensors", Med. Eng. Phys., vol. 29, No. 10, pp. 1084-1088 (2007).

\* cited by examiner

*Primary Examiner* — Maureen Wallenhorst
(74) *Attorney, Agent, or Firm* — Judy M. Mohr; Jacqueline F. Mahoney; McDermott Will & Emery LLP

(57) ABSTRACT

Devices, methods and systems effective to evaluate a physical or chemical property of an ion exchange resin-treated biological fluid sample are provided.

20 Claims, 14 Drawing Sheets

METHODS, SYSTEMS AND DEVICES FOR ANALYZING A BIOLOGICAL FLUID SAMPLE FOLLOWING ION EXCHANGE

CROSS REFERENCE TO RELATED APPLICATIONS

This application is a U.S. National Stage of International Patent Application No. PCT/US2009/003146, filed May 20, 2009, which claims the benefit of U.S. Provisional Application No. 61/128,280 filed May 20, 2008, all of which are hereby incorporated by reference.

TECHNICAL FIELD

The present subject matter relates to methods, systems and devices effective to measure a physical or chemical property of a biological fluid sample, where the sample is exposed to an ion exchange medium prior to sample analysis.

BACKGROUND OF THE TECHNOLOGY

A variety of chemical and physical parameters of biological fluids are routinely analyzed in the diagnosis of disease and in routine monitoring of medical conditions. Many biological fluids must be processed prior to analysis to remove interfering proteins, biomolecules, or bulk properties of the sample. This can present difficulties in obtaining and validating the results obtained from biological sample analysis. Reliability and reproducibility of data is critical. Hence, simple sample preparation methods that yield accurate, reliable and reproducible results are highly desirable.

The sample preparation process has a direct impact on such analyses in terms of accuracy, precision, and quantitation limits. Effective sample preparation is extremely important to the analytical process. Optimally, the sample preparation process is relatively fast, easy, and an inexpensive means to obtain accurate and consistent results when analyzing a chemical or physical parameter of a biological fluid.

Non-invasive sample collection alternatives that reduce or eliminate the skin trauma, pain, infection risk and blood waste associated with traditional blood tests are also preferred.

Salivary diagnostics is an emerging field that relies on saliva as an easily-obtainable biological fluid for detection or diagnosis of various diseases and medical conditions. Unprocessed saliva is a viscous inconsistent fluid with unusual shear properties and which contains a number of proteins. These properties of saliva make it difficult to analyze bulk properties of saliva. Laboratory techniques such as solvent extraction, centrifuge filtration and/or relatively long periods of settling in sealed containers are often used to make saliva more amenable to subsequent analysis.

A noninvasive means to evaluate chemical or physical parameters of biological fluids, such as saliva, that is portable, simple, rapid to use, and which provides accurate, reliable and reproducible results is highly desirable. The present methods and systems address this need.

BRIEF SUMMARY

In one aspecit, methods for measuring a physical or chemical property of a biological fluid are provided. The methods comprise providing a biological fluid sample; treating the sample with an ion exchange medium; further providing a sensor comprising a hydrogel having a physical or chemical property, wherein an initial value of the physical or chemical property is known and the hydrogel is characterized by a change in the physical or chemical property in response to exposure to an ion exchange medium-treated biological fluid sample; contacting the hydrogel with the ion exchange medium-treated biological fluid sample; evaluating the change in the hydrogel; and correlating the change in the hydrogel with a physical or chemical property of the biological fluid.

Exemplary biological fluids include saliva, whole blood, plasma, serum, lymph, synovial fluid, peritoneal fluid, pleural fluid, urine, sputum, semen, vaginal lavage, bone marrow, cerebrospinal cord fluid and tears.

Exemplary physical properties include absorption at a given wavelength, density, electric conductivity, pH, osmolality, osmolarity, thermal properties, viscosity, dielectric constant, refractive index and light scattering.

Exemplary chemical properties include the concentration of glucose, creatinine, urea, cortisol, total protein, total electrolytes, estrogen, progesterone, testosterone, a cation, e.g., sodium ($Na^+$); calcium ($Ca^{2+}$); potassium ($K^+$), or magnesium ($Mg^{2+}$), an anion, e.g., chloride ($Cl^-$); fluoride (Fl); bromide (Br); sulfate ($SO_4^{2-}$ nitrate ($NO_3^-$); carbonate ($CO_3^{2-}$); and bicarbonate ($HCO_3^-$).

The measured change in a physical or chemical property of the hydrogel is typically a change in volume, a change in optical density, a change in refractive index, a change in AC conductivity or capacitance.

Exemplary hydrogels are cross-linked and have a net negative charge, e.g., a cross-linked hydrogel comprised of an acrylamide moiety, a hydroxyalkyl acrylate or a hydroxyalkyl methacrylate, vinyl ether, or vinyl pyrrolidone which comprises an anionic moiety selected from a carboxylate group, a sulfate group, a sulfonate group and a phosphate group.

In some embodiments, the ion exchange material is a cation exchange resin and/or a chelating resin, which may comprise an iminodiacetic acid functionality.

In other embodiments, the ion exchange material is selected from the group consisting of a water insoluble polymeric cation exchange resin, EDTA, oxalic acid, citric acid and a water soluble polyacrylate.

Exemplary ion exchange media are selected from the group consisting of anion exchange media, cation exchange media and mixed ion exchange media, preferably cation exchange or mixed ion exchange media. A preferred ion exchange media is a proton, sodium, or potassium form cation exchange media in the form of a water insoluble resin.

In one preferred embodiment, the biological fluid is saliva, the measured physical property is osmolality, the ion exchange medium is a cation exchange or chelating resin and the measurement is based on a change in volume of the hydrogel. In one embodiment, treating a biological fluid sample with an ion exchange medium is effective to remove $Ca^{2+}$ from the biological fluid.

In one embodiment, treating a biological fluid sample with an ion exchange medium is effective to remove $Ca^{2+}$ and/or $Mg^{2+}$ from the biological fluid.

In another aspect, hydrogel sensor systems and devices for measuring a physical or chemical property of a biological fluid sample are provided. The hydrogel sensor systems typically comprise a cartridge for collecting and treating a biological fluid sample with an ion exchange medium and a means for attachment to a device comprising a hydrogel sensor effective to measure a physical or chemical property of the biological fluid. The device typically comprises a movable microcantilever sensor having a known resistance corresponding to an initial position of the tip of the microcantilever. The cantilever may be free standing with a hydrogel layer disposed on one side or may comprise a hydrogel secured to a rigid substance and positioned against the microcantilever, wherein the change in a physical property of the hydrogel deflects the microcantilever and a signaling component which creates a detectable signal in response to movement of the microcantilever. In another embodiment the hydrogel sensor system may comprise a hydrogel contacting a pressure sensor or disposed on a reflective surface.

In some embodiments, the sensor is disposable.

BRIEF DESCRIPTION OF THE DRAWINGS

The methods and systems are best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

A. Introduction

Figure 1:
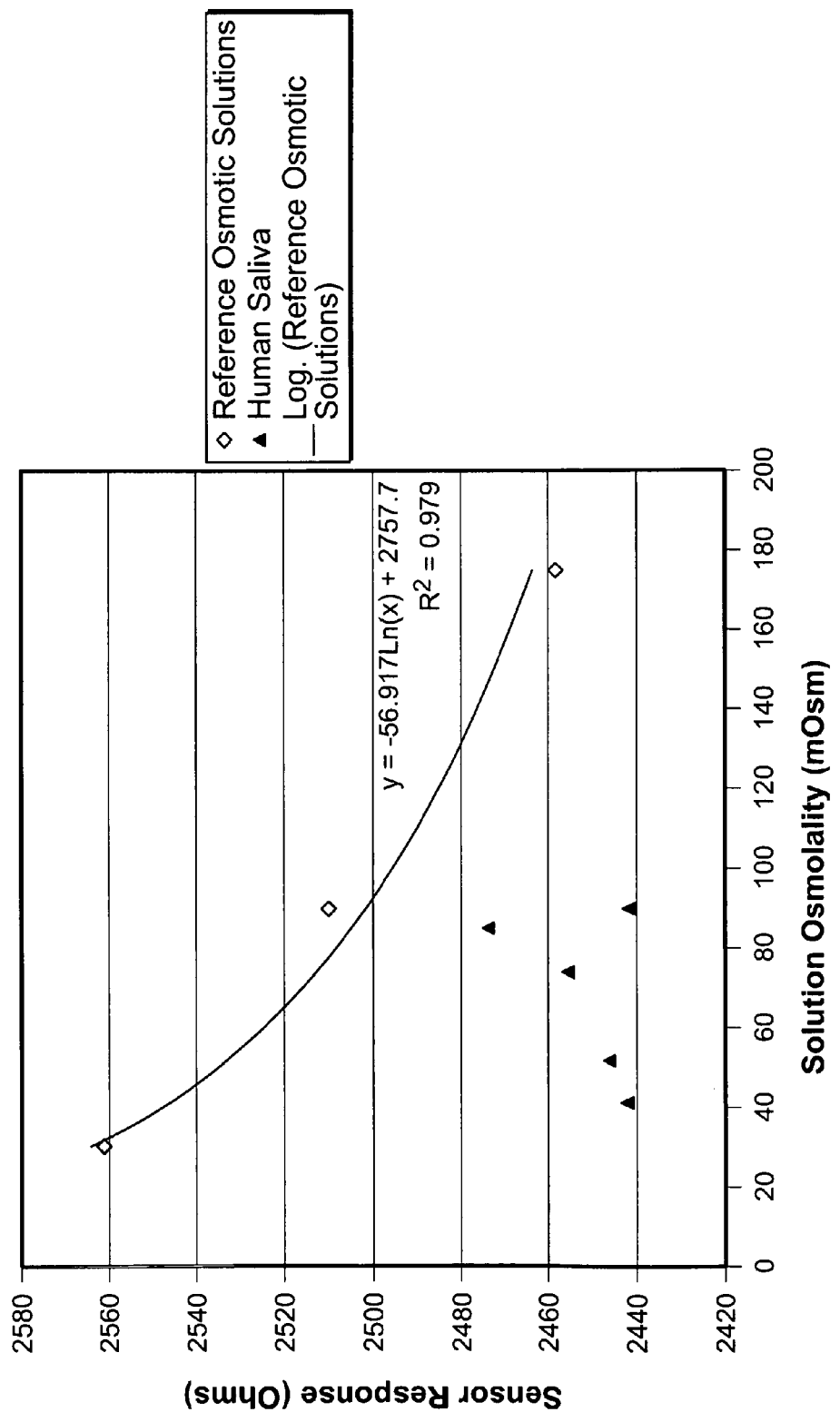
FIG. 1 is a graphic depiction of cantilever resistance (Ohms) versus solution osmolality (mOsm), for reference NaCl solutions and human saliva samples.

Compositions, devices, methods and systems for determining a physical or chemical property of a biological fluid using a device are provided. Methods for treating the biological fluid are provided such that the interference of substances found in the biological fluid with the accuracy of the physical or chemical property determination is minimized or eliminated. Following treatment, the biological fluid sample is put in contact with a hydrogel which acts as a sensing material on a detecting device. The hydrogel undergoes a physical or chemical change, e.g., volumetric expansion or contraction in response to a physical or chemical property of the biological fluid. The change is correlated with a physical or chemical property of the biological fluid. The change may be qualitative or quantitative. The device records and displays the results of the change, such that a physical or chemical property of the biological fluid is measured.

The following disclosure describes the compositions, methods, systems and kits which constitute the invention. The invention is not limited to the specific, devices, methodology, systems, kits or conditions described herein, as such may, of course, vary. It is also to be understood that the terminology used herein is for the purpose of describing particular embodiments only, and is not intended to limit the scope of the present invention.

As used herein and in the appended claims, the singular forms "a", "and", and "the" include plural references unless the context clearly dictates otherwise.

Unless defined otherwise, all technical and scientific terms used herein generally have the same meaning as commonly understood to one of ordinary skill in the art to which this invention belongs. Although any methods, devices and materials similar or equivalent to those described herein can be used in the practice or testing of the invention, the preferred methods, devices and materials are now described.

The publications discussed herein are provided solely for their disclosure prior to the filing date of the present application. Nothing herein is to be construed as an admission that the invention is not entitled to antedate such a disclosure by virtue of prior invention.

B. Definitions

The terms "ion exchange medium", "ion exchange material" and "ion exchange resin" are used interchangeably herein with reference to any material effective to remove ionic components of a biological fluid sample which interfere with the analysis of a physical or chemical property thereof, e.g., removal of divalent cations such as calcium from a biological fluid sample. An "ion exchange" medium may be provided as a resin, on a dipstick, paper, in a cartridge, tube, pipe, syringe, or in any manner that an ion exchange medium may be exposed to a biological fluid sample in a manner effective to remove interfering ionic components of the biological fluid sample prior to analysis.

The term "biological fluid" is used herein with reference to a biological fluid taken from a subject selected from the group consisting of saliva, whole blood, plasma, serum, lymph, synovial fluid, peritoneal fluid, pleural fluid, urine, sputum, semen, vaginal lavage, bone marrow, cerebrospinal cord fluid and tears. Frequently the sample will be a "clinical sample" which is a sample derived from a patient.

The term "chemical property" is used herein with reference to a property of a biological fluid that becomes evident during a chemical reaction or the amount of a particular chemical entity in a biological fluid.

The term "MEMS" or "Micro-Electro-Mechanical Systems" provide for the integration of mechanical elements, sensors, actuators, and electronics on a common silicon substrate through microfabrication technology.

The term "physical property" is used herein with reference to any aspect of a biological fluid that can be measured, evaluated or observed without changing the sample.

The term "osmolality" is used herein with reference of the osmoles of solute per kilogram of solvent. An osmole (Osm) is a unit of measurement that defines the number of moles of a chemical compound that contribute to a solution's osmotic pressure. In the laboratory setting, osmolality is commonly measured using an osmometer and the freezing point depression method. One mole (the molecular weight in grams) of any substance dissolved in one kilo of water will cause an osmotic pressure of 17,000 mmHg, a boiling point elevation of 0.52° C., a vapor pressure decrease of 0.3 mmHg and a freezing point depression of −1.86° C. and corresponds to an osmolality of 1000 mOsmols per kilo of water (1000 mOsmols). Using the freezing point depression method, 1 mOsmol will produce a temperature change of only 0.0018° C.

The term "osmolarity" is used herein with reference to the osmoles of solute per liter of solution. Molarity and osmolality are not commonly used in asymmetry because they are temperature dependent; and water changes its volume with temperature.

The terms "phase change" and "phase transition" are used interchangeably herein and include evaporation, melting and freezing of water, the formation of frost and snow, and the sublimination of dry ice which are well-known phenomena, and are examples of five of the six common changes in state: (i) melting of a solid into a liquid; (ii) freezing of a liquid into a solid; (iii) evaporation of a liquid into a gas; (iv) condensation of a gas into a liquid; (v) the vaporization (sublimination) of a solid into a gas; and (vi) the freezing of a vapor into a solid. The changes are listed in parts in which each process of the pair is the reverse of the other. When the substance has polymorphic solid forms such as a hydrogel, other phase transitions are possible. Such transitions are described in US Patent Publication No. 20070249059 (expressly incorporated by reference herein).

The term "melting point" is used herein with reference to another phase change of interest in polymeric systems. Because polymers are usually statistical mixtures of individual components they typically have broader melting point ranges than pure elements or compounds. Melting points of polymers, including gels, can be measured by calorimetric methods, for example differential scanning calorimetry, or by optical methods or mechanical methods.

The term "microcantilever" is used herein with reference to a device that can act as a physical or chemical sensor by detecting changes in cantilever bending or vibration frequency. Adsorption stress on one side of the cantilever can be used as a means of detecting a physical or chemical property, e.g., the swelling or shrinking of a hydrogel. Depending on the nature of the change in the hydrogel, the deflection can be up or down. The deflection is proportional to the change. Microcantilevers are micro-electromechanical systems (MEMs) that can be micromachined and mass-produced from single crystal silicon wafers or similar material including SU8 resin. Microcantilevers offer high sensitivity and selectivity for a wide variety of biological and chemical sensing.

As used herein the term "piezoresistive" refers to a material having an electrical resistance which decreases in response to compression caused by mechanical pressure applied thereto in the direction of the current path. Such piezoresistive materials can be, for example, resilient cellular polymer foams with conductive coatings covering the walls of the cells, or elastomers containing conductive particles. As a piezoresitive microcantilever deflects, it undergoes a strain that will apply stress to a piezoresistor element, thereby causing a change in resistance that can be measured by electronic means. One advantage of the piezoresistive method is that the readout system can be integrated on a chip.

The term "resistance" refers to the opposition of the material to the flow of electric current along the current path in the material and is measured in ohms. Resistance increases proportionately with the length of the current path and the specific resistance, or "resistivity" of the material, and it varies inversely to the amount of cross sectional area available to the current. The resistivity is a property of the material and may be thought of as a measure of (resistance/length)/area. More particularly, the resistance may be determined in accordance with the following formula:

$$R=(rho*L)/A \tag{I}$$

where: R=resistance in ohms; rho=resistivity in ohm-inches; L=length in inches; and A=area in square inches. The current through a circuit varies in proportion to the applied voltage and inversely with the resistance, as provided in Ohm's Law:

$$I=V/R \tag{II}$$

where I=current in amperes; V=voltage in volts; and R=resistance in ohms.

C. Ion Exchange Media

Provided herein are ion exchange media useful for removal of a components of a biological fluid sample that if not removed may interfere with the determination of a chemical or physical property thereof. For example, a potentially interfering component of a biological fluid sample having a basic group such as an amino group can complex with an ion-exchange resin that bears an acidic group such as a sulfate or carboxylate group. Conversely, a potentially interfering component of a biological fluid sample that has an acidic group can complex with an ion-exchange resin that bears a basic group.

There are a number of proteins in saliva, e.g., mucin, which can interfere with analysis of biological fluids. Mucin is a heavily glycosylated protein. Proteins such as mucin associate into multi-molecular networks mediated by calcium ions. In preparing saliva samples for analysis, it is necessary to process samples such that stable readings and accurate and reproducible results are obtained. While not wishing to be bound by theory, as described in the examples provided below, application of techniques for removal of potentially interfering proteins and associated calcium ions is effective to obtain stable readings and accurate and reproducible results using a device which relies on a hydrogel sensor.

The present subject matter relates to a process for removing interfering materials from biological fluid samples prior to analysis. In one exemplary approach, complexed or chelated cations are removed from a biological fluid sample using an ion exchange medium, such as an ion exchange resin.

Ion-exchange resins are water-insoluble materials, often cross-linked polymers, containing covalently bound salt forming groups in repeating positions on the polymer chain. The ion exchange medium may be synthetic (e.g., polymers or copolymers of acrylic acid, methacrylic acid, sulfonated styrene, sulfonated divinylbenzene), or partially synthetic (e.g., modified cellulose and dextrans). The ion exchange may also be inorganic, e.g., silica gel, or aluminosilicates, in the native state or modified by the addition of ionic groups.

The charge on the functional group determines the type of ions which can be attracted by the resin. For example, some cationic resins typically contain sulfonic acid groups which are negatively charged and thus attract positively charged cations. Some anionic resins contain amine-based functional groups which are positively charged and thus attract anionic groups.

Cation exchange resins can be used to remove cations from solution when the complex is disrupted with subsequent acid treatment. For example, Amberlite® IRC-718 chelating resin (Rohm and Haas), has an iminodiacetic acid functionality and selectively complexes the divalent metal-ions, $Fe^{2+}$, $Cu^{2+}$, $Zn^{2+}$, and $Ni^{2+}$. See, e.g., Raynal, T. et al., J Biol. Chem. 2003 Aug. 1; 278(31):28703-10.

In another embodiment, SACMP, a strong acid cation exchange resin available from Resintec is converted from the hydrogen form via exchange with a sodium solution yielding the sodium form and then utilized to remove calcium from saliva.

Anion exchangers can be classified as weak or strong. As used herein, a weak anion exchange medium" or "weak cationic exchanger" is one where the charge group is a weak base, which becomes deprotonated and, therefore, loses its charge at high pH. A "strong anion exchanger" on the other hand, acts as a strong base, which remains positively charged throughout the pH range of 1-14.

Cation exchange media can also be classified as either weak or strong. A "strong cation exchange medium" or "strong cation exchanger" contains a strong acid (such as a sulfopropyl group) that remains charged from pH 1-14; whereas a "weak cation exchange medium" or "weak cationic exchanger" contains a weak acid (such as a carboxymethyl group), which gradually loses its charge as the pH decreases below 4 or 5.

Any type of ion-exchange material can be used to process a biological fluid sample prior to analysis, dependent upon the nature of the sample component which interferes with the analysis and must therefore be removed prior to sample analysis.

Specific examples of cationic ion exchange resins include, but are not limited to: AMBERJET™ 1200(H); Amberlite™ CG-50, IR-120 (plus), IR-120 (plus) sodium form, IRC-50, IRC-50S, and IRC-718; Amberlyst™ 15, 15 (wet), 36 (wet), A-21, A-26 borohydride, bromide, chromic acid, fluoride, and tribromide; and DOWEX™ 50WX2-100, 50WX2-200, 50WX2-400, 50WX4-50, 50WX4-100, 50WX4-200, 50WX4-200R, 50WX4-400, HCR-W2, 50WX8-100, 50WX8-200, 50WX8-400, 650C, MARATHON™ C, DR-2030, HCR-S, MSC-1, 88, CCR-3, MR-3, MR-3C, Fiban™ and Retardion™.

Specific examples of anionic ion exchange resins include, but are not limited to: AMBERJET™ 4200(Cl); Amberlite™ IRA-67, IRA-400, IRA-400(Cl), IRA-410, IRA-743, IRA-900, IRP-64, IRP-69, XAD-4, XAD-7, and XAD-16; AMBERSORB™ 348F, 563, 572 and 575; DOWEX™ 1X2-100, 1X2-200, 1X2-400, 1X4-50, 1X4-100, 1X4-200, 1X4-400, 1X8-50, 1X8-100, 1X8-200, 1X8-400, 21K Cl, 2X8-100, 2X8-200, 2X8-400, 22 Cl, MARATHON™ A, MARATHON™ A2, MSA-1, MSA-2, 550A, 66, MARATHON™ WBA, and MARATHON™ WGR-2; and Merrifield's peptide resins.

The size of the ion-exchange particles is typically less than about 2 millimeters, preferably less than about 1000 microns, more preferably less than about 500 microns, more preferably less than about 150 micron (about 40 standard mesh). Commercially available ion-exchange resins (including Amberlite™ IRP-69, INDION™ 244 and INDION™ 254 and numerous other products) are typically available in several particle size ranges, and many have an available particle size range of less than 150 microns.

The particle size is not a critical variable. Ion exchange resins have pores of various sizes, which expand the area available for active agent binding. The typical pore diameter is in the range of about 30 to 300 nanometers (nm); however, resins with larger pores, such as 500 to 2000 nm (0.5 to 2 micron), may also be used.

The final concentration of the ion exchange medium is dependent on the type of sample to be treated and the ion exchange capacity of the ion exchange media, but must be sufficient to effectively remove the potentially interfering ions in the sample to be analyzed.

The capacity of ion exchange media can vary significantly and is generally defined in terms of milliequivalents (meq) per gram of dry resin. In a preferred embodiment the ion exchange resin is equilibrated with water before being contacted with the sample to be analyzed. The minimum amount of ion exchange media required can be calculated by measuring or estimating the typical composition of the sample to be treated and then calculating the amount of ion exchange media required to effectively treat a sample of a specific size. In the case of removing calcium from saliva, for example, it is known that saliva contains approximately 2 millimol/L of calcium. Accordingly, a 1 ml sample of saliva will require sufficient ion exchange media to remove 0.002 millimole of calcium.

One preferred ion exchange media for treating saliva is Amberlite 748, a chelating type ion exchange media which has an exchange capacity of 4.4 meq/g. Accordingly, 1 ml of saliva would require a minimum of 2 mg of resin. In general, it is advantageous to utilize an excess of ion exchange resin. Typically, a 5 fold excess to a 20 fold excess is employed when processing a biological fluid sample prior to analysis. Other preferred ion exchange media for treating saliva include Fiban, a fiber based ion exchange media and ion exchange filter paper or fibers or powder prepared from functionalized cellulose.

D. Methods and Compositions for Measuring a Physical or Chemical Property of a Biological Fluid Provided herein are compositions and methods for measuring a physical or chemical property of a biological fluid collected from a subject. In carrying out the method: (1) a biological fluid is collected from a subject; (2) the biological fluid is treated with an ion exchange medium; (3) a device comprising a hydrogel sensor having a known physical or chemical property is provided, wherein the initial value for the physical or chemical property of the hydrogel is known; (4) the ion exchange material-treated sample is placed in contact with the hydrogel sensor; (5) the physical or chemical property of the hydrogel sensor is evaluated following exposure to the ion exchange material-treated sample, for example, a change in volume, or a change in an electrical property, e.g., AC conductivity, capacitance or resistance of the hydrogel; and (6) the change in a physical or chemical property of the hydrogel sensor is correlated with a particular physical or chemical property of the biological fluid sample.

Any means of sample collection and ion exchange medium treatment may be used to prepare a biological fluid sample for analysis. The sample collection vessel is typically disposable, contains a predetermined amount of ion exchange medium and is designed for collection of a predetermined sample volume. A sample volume is typically from about 150 to 250 microliters (uLs), but as one of skill in the art will understand, the sample size may vary and can be significantly greater or less than 200 uLs dependent upon the reaction conditions. Prior to carrying out sample analysis, ion exchange medium treatment of a biological fluid sample typically involves exposure of the ion exchange medium to the sample under conditions that allow the biological fluid sample and the ion exchange medium to reach equilibrium, such that interfering ionic materials are removed from the sample prior to analysis.

In carrying out the analysis of a biological fluid sample, the sensor comprises a detecting means such as an optical refractometer, an interferometer or one or more electric circuits which can detect a change in a measurable physical property or properties of the hydrogel. In a specific embodiment the volume of the hydrogel is monitored with a microcantilever. A particular physical or chemical property of the sensor may be measured prior to and after the introduction of a biological fluid sample to the sensor and the results compared to detect a change and the degree of change in the physical property or properties of the microcantilever. The change itself can then be associated with, for example the osmolality of a saliva sample. In this exemplary application of the claimed methods, the degree of change corresponds to the degree of microcantilever arm deflection which, in turn, corresponds to the osmolality of the saliva sample.

The device includes a means for detecting a change in a measurable physical or chemical property of the sensor. As will be understood by those of skill in the art, resistance is one example of a measurable physical property used to detect a change in the microcantilever. Other examples include, but are not limited to optical transmittance (optical density), refractive index and AC conductivity, which vary in response to chemical or physical changes of the hydrogel.

E. Chemical and Physical Properties of a Biological Fluid

The methods and devices described herein find utility in measurement of any chemical or physical property of a biological fluid that may be determined using a sensor comprising a hydrogel.

Exemplary chemical properties are selected from the group consisting of the concentration of a particular component such as glucose, creatinine, urea, cortisol, total protein, total electrolytes, total estrogen, total progesterone total testosterone, a cation, e.g., sodium ($Na^+$); calcium ($Ca^{2+}$); potassium ($K^+$), or magnesium ($Mg^{2+}$); an anion, e.g., chloride ($Cl^-$); fluoride (Fl); bromide (Br); sulfate ($SO_4^{2-}$); nitrate ($NO_3^-$); carbonate ($CO_3^{2-}$); bicarbonate ($HCO_3^-$); or a known biomarker.

Exemplary physical properties are selected from the group consisting of absorption at a given wavelength, density, electric conductivity, pH, osmolality, osmolarity, thermal transfer, viscosity, dielectric constant, refractive index or light scattering.

F. Saliva

Saliva is an excellent biological fluid for analysis. It is easily collected using noninvasive techniques and samples can readily be collected at multiple time points.

Analyzing saliva is similar to analyzing blood serum or plasma, due to its protein content and other potential contaminants.

While not wishing to be bound by theory, there are a number of proteins in saliva, e.g., mucin, which can interfere with analysis of biological fluids. When saliva mimic solutions or saliva analogues are formulated to contain mucin, the mucin interferes with hydrogel sensor behavior, suggesting that mucin may interfere with accurate analysis of saliva samples. Mucins are a family of heavily glycosylated proteins secreted by mucosal surfaces and mucin is largely responsible for the viscosity and "stringiness" of human saliva. Mucins are relatively abundant, but in widely varying concentration in human saliva.

In preparing saliva samples for analysis, it is necessary to process samples such that stable readings and accurate and reproducible results are obtained. As described in the examples provided below, the treatment of biological fluid samples such as saliva with an ion exchange medium was effective to yield stable and consistent results using the hydrogel sensors described herein.

A hydrogel sensor for use in a device for measuring saliva osmolality typically comprises a hydrogel responsive to a change in osmolality in the range of 50-250 mOsm.

G. Devices for Measuring Physical and Chemical Properties of a Biological Fluid

The claimed methods for evaluating a chemical or physical property of an ion exchange medium-treated biological fluid are typically accomplished using a device which comprises a highly sensitive and selective sensor. The device is comprised of a sensor material secured into a fixed position on a substrate, a deformable arm and a signaling component which creates a detectable signal in response to movement of the arm. The sensitivity of the device is enhanced by using a sensor material, e.g., a hydrogel, which undergoes a dramatic change in volume such as a phase change in response to a target molecule of interest. A change in volume of the sensor material takes place in response to the presence of a particular chemical entity, pH, osmolality, temperature change or other variation in the environment of the hydrogel which moves the arm causing the signaling component (e.g. a piezoresistor) to create a detectable signal (e.g. change in resistance) thereby indicating the presence/amount of the chemical or osmoles in the ion exchange medium-treated biological fluid.

The methods and devices described herein provide a means for evaluating a chemical or physical property of an ion exchange medium-treated biological fluid by contacting the ion exchange medium-treated biological fluid with a hydrogel sensor. In one embodiment, located adjacent to and in contact with the hydrogel sensor is a deflectable arm of a microcantilever. In another embodiment, in the presence of a particular chemical of interest in the ion exchange medium-treated biological fluid sample, the hydrogel sensor undergoes a change in volume wherein expansion causes the deflectable microcantilever arm to deflect upward. In yet another embodiment, the hydrogel undergoes a physical or chemical change other than a volumetric change (i.e. other than swelling or shrinking). Examples of which include changes in AC conductivity, capacitance, ionic mobility, resistance, optical transmittance, fluorescence, refractive index or a viscoelastic property of the hydrogel.

Alternatively, in another embodiment, in response to a particular physical property of the ion exchange medium-treated biological fluid sample, the hydrogel undergoes a volumetric contraction resulting in a downward displacement of the deflectable arm of the microcantilever. Devices for evaluating a chemical or physical property of a ion exchange medium-treated biological fluid are described for example in United States Patent Publication No. 20070249059, expressly incorporated by reference herein.

In one embodiment, the hydrogel is disposed on one side of a microcantilever. In another embodiment the microcantilever is formed on a substrate separate from the surface including the sensing material. Conventional semiconductor processing technology may be used to form the microcantilever. Various configurations and orientations of the microcantilever may be used. The microcantilever includes an overhang portion which extends over the edge of the microcantilever substrate and allows for the substrate and the surface containing the sensing material to be positioned in close proximity to one another such that the deflectable arm of the microcantilever is situated above and in contact with the sensing material. A micromanipulator may be used to position and align the components. The deflectable arm of the microcantilever includes at least one measurable physical property which changes when the deflectable arm deflects in response to a volumetric change of the hydrogel sensor. The devices described herein also provide a detecting means in the form of various electric circuits which detect a change in position of the deflectable arm.

The microcantilever may be calibrated to correlate a measured change in the ion exchange medium-treated biological fluid sample with a chemical or physical property of the biological fluid. In the case where the chemical or physical property of the biological fluid is not detectable, e.g., a specific chemical analyte is not present, the microcantilever will not deflect and therefore the measurements taken before and after the introduction of the ion exchange medium-treated biological fluid sample will be substantially the same.

One preferred sensor is a micro-electro-mechanical systems (MEMS) device comprising a piezoresistive microcantilever 20 μM wide, 300 μM long and 3 μM thick and surrounding die, and wire-bonded connector and female pin block. Nominal resistance across the cantilever is 2.2 kOhms and increases approximately 1 Ohm for each micron the cantilever tip is deflected from neutral. In this embodiment, a hydrogel is secured to a rigid substrate and positioned against the microcantilever such that swelling of the hydrogel deflects the micro-cantilever.

The device further comprises a signaling component which undergoes a change such as a change in resistance, resonant frequency, electrical output, or capacitance in response to very small movements of the microcantilever arm, or in the case of a resonator, to the rheological properties of the materials it is contact with.

H. Hydrogels

During the detection process, the sensor material undergoes a change in volume whereby a hydrogel sheet of, for example a thickness of about 5, 10, 20, 50 or 100 microns expands or contracts 0.5% or more, 1% or more, 5% or more, or 10% or more and is detected by the arm capable of detecting movement of in a range of 1 to 1,000 angstroms or more which may include a phase change.

Hydrogels are three dimensional networks of hydrophilic polymers which are crosslinked to form water-swellable but water insoluble structures. The term hydrogel is to be applied to hydrophilic polymers in a dry state (xerogel) as well as in a wet state. These hydrogels can be crosslinked in a number of ways, as described for example in United States Patent Publication No. 20070249059, expressly incorporated by reference herein. Alternatively, hydrogels may be crosslinked with ionic species or by incorporation of self associating monomers resulting in physical crosslinking or may be effectively be rendered insoluble by incorporation into an interpenetrating network.

Exemplary hydrogel chemical sensor materials include partially hydrolyzed poly(vinyl acetate) (PVA), poly(ethylene vinyl acetate) (PEVA), modified PEVA, poly(4-vinylphenol), poly(styrene-co-allyl alcohol), poly(N-vinylpyrrolidone), poly (alkylethers) including poly(ethylene oxide) and poly(ethylene oxide) co-polymers poly(vinylethers), poly (hydroxyalkylacrylates) or methacrylates or acrylamides including hydroxyethylacrylate, and hydroxypropyl acrylate, substituted or unsubstituted acrylamide or methacrylamide, including n,n-dimethylacrylamide, n-isopropylamide and other known hydrogels.

On example of the basic construction of a fully functional sensor involves determining the neutral resistance of the sensor, then affixing a substrate and hydrogel to the die such that the hydrogel deflects the cantilever as it swelled. In this exemplary approach, hydrogel polymers may be drawn and cured as fibers with approximately 25 μM diameter, cut to approximately 200 μM long sections, and cured on a silane treated silicon wafer fragment. This fragment is then affixed against the sensor die with epoxy to create a "hydrogel fiber sensor".

Alternatively, the surface of silane treated silicon wafers may be coated with a hydrogel polymer solution in an even continuous layer; achieved by way of natural surface tension of poured polymer, spin coating, or surface repulsion from the low-surface-energy side of Mylar film placed on top of the wet hydrogel polymer. Hydrogel sensors can also readily be prepared using photolithographic methods.

I. Utility

In general, biological fluids must be processed prior to analysis to remove interfering proteins or other biomolecules. The processing step can present difficulties in obtaining accurate and consistent results in analysis of biological samples. Given that reliability and reproducibility of data is critical, simple and effective sample preparation methods that reduce data error are highly desirable.

A noninvasive means to evaluate chemical or physical parameters of biological fluids that is portable, simple and rapid to use, and which provides accurate analytical results is also desirable. Accordingly, there is utility in the claimed devices, methods and systems for analyzing a physical or chemical property of a biological fluid sample using a hand-held device comprising a microcantilever-based sensor system. The present invention addresses this need.

The ocular surface requires a complete tear film to maintain health and function. Adequate production, retention, and balanced elimination of tears is necessary for this process. Any imbalance of these components can lead to the condition of dry eye. A single biophysical measurement that captures the balance of inputs and outputs from the tear film dynamics is tear osmolality. It has been suggested that tear hyperosmolality is the primary cause of discomfort, ocular surface damage, and inflammation in dry eye. Hyperosmolality can result from either a decrease in tear secretion or an increase in tear evaporation, the two pathways that produce ocular dryness. Hence, hyperosmolarity is believed to be a feature common to all cases of dry eye disease.

A need exists to rapidly and accurately measure properties of tear film, including osmolality. Measurement of tear film osmolality is therefore a convenient and non invasive diagnostic assay. A convenient tear film osmometer was constructed by coating microfiber cation exchange resin onto a microcantilever sensor as described in Example 3.

A serum or blood osmolality test measures the amount of chemicals dissolved in the liquid part of the blood. Chemicals that affect serum osmolality include sodium, chloride, bicarbonate, proteins, and sugar (glucose). A serum osmolality test is done on a blood sample taken from a vein or finger stick. Serum osmolality is measured to: (1) check the balance between the water and the chemicals dissolved in blood; (2)

determine if severe dehydration or overhydration is occurring; (3) evaluate antidiuretic hormone (ADH) production by the hypothalamus; (4) determine the cause of seizures or coma, which may be caused by an imbalance between water and electrolytes in the body; (5) determine if a person has swallowed certain poisons. The normal values in serum are 280 to 295 mOsm/L or about 280 to 303 milliosmoles per kilogram (mOsm/kg).

A higher-than-normal serum or blood osmolality level may indicate: (a) dehydration; (b) diabetes insipidus; (c) hyperglycemia; (d) hypernatremia; (e) consumption of methanol; (f) consumption of ethylene glycol; (e) renal tubular necrosis; (f) stroke or head trauma resulting in deficient ADH secretion (cranial diabetes insipidus); of (g) uremia. A lower-than-normal osmolality level may indicate: (a) excess fluid intake; (b) hyponatremia; (c) overhydration; (d) paraneoplastic syndromes associated with lung cancer; or (e) syndrome of inappropriate ADH secretion.

Osmolality of whole blood and serum are commonly measured using a freezing point or vapor pressure osmometer. The claimed sensors were used to effectively measure the osmolality of whole blood as described in Example 3.

The methods and systems are described by reference to the following examples, which are offered by way of illustration and are not intended to limit the invention in any manner. Standard techniques well known in the art or the techniques specifically described below are utilized. Therefore, the description and examples should not be construed as limiting the scope of the invention, which is delineated by the appended description of exemplary embodiments.

EXAMPLES

Materials and Methods

A. Preparation of Sensing Hydrogels

An osmotic responsive hydrogel precursor was prepared by polymerizing a mixture of hydroxypropyl acrylate, acrylamide and acrylic acid in the ratio of 85:15:1. The polymerization was carried out in a 70:30 w/w mixture of water and dimethyl formamide utilizing azobisisobutylnitrile (Aldrich Chemical) as initiator. The resulting polymer was utilized as is or purified by washing with hot water. One type of sensor material was prepared by combining the hydrogel precursor with a crosslinking agent and casting a film on a substrate or drawing fibers and subsequently drying and curing the material. Examples of suitable curing agents include aminoplast resin such as Cymel 327 (Cytec), polyazyridines (Cytec), multivalent metal ions such as zinc or zirconium, multifunctional isocyanates, multifunctional aziridines such as CX-100 (DSM) or a wide range of other commercially available reactive curing agents. Alternatively, a hydrogel was formed in place by polymerizing a mixture of hydrogel precursor monomers including a minor amount of a multifunctional monomer, for example ethyleneglycol diacrylate, hexanediol diacrylatge, or other multifunctional materials (for example, the material provided by Cytec under the trade name Ebercryl or by Sartomer). A convenient method of producing a sensor relies on use of a photomask and ultraviolet light to selectively crosslink or polymerize precursor materials to produce hydrogels of a specific thickness, shape and size.

The preparation of hydrogel based sensors is described in a number of publications including US Patent Publication No. 20050164299; Trinh et al, Electronics System Integration Technology Conference, September 2006, Volume 2: 1061-1070; Sorber et al., Anal Chem. 2008 Apr. 15; 80(8):2957-62. Epub 2008 Feb. 28; and Richter et al., "Review on Hydrogel-based pH Sensors and Microsensors" in *Sensors*, 2008, 8: 561-581 (see pages 566-571); each of which is expressly incorporated by reference herein.

Sensors for measuring osmolality were constructed utilizing peizoresistive microcantilevers (Cantimer, Inc., Menlo Park Calif.). The cantilevers utilized have approximate dimensions of 200 microns long×20 microns wide by 3 microns thick. A second silicon substrate pattern was coated via UV lithography with hydroxypropyl acrylate based hydrogel discs of approximately 25 microns thick and 100 micron diameter. The coated substrate was singulated and bonded to the cantilever substrate using a photocurable epoxy resin such that about ¼ of the cantilever was in contact or directly above the hydrogel. Sensors were equilibrated in 50 mOsmol sodium chloride solution adjusted to pH 9 and then rinsed in deionized water prior to use. Baseline cantilever resistance for each sensor was measured and calibration curves prepared by exposing the sensor to a range of buffered salt solutions.

B. Measuring Solution Osmolality

Solution osmolality measurements were carried out by filling a 1.7 mL VWR microcentrifuge tube with 1 mL of analyte, and placing it in a flow-through temperature controlled block, hooked to a Fischer Scientific 9110 recirculating chiller filled with distilled water. Unless otherwise stated, the recirculating chiller was set to maintain a temperature of 25° C. The sensor was connected to a wiring harness, which descended into a microcentrifuge tube seated in a temperature control block. Foam insulation placed around the block provided for additional thermal control.

A hydrogel sensor was placed in a fluid sample such that the entire die was submerged. The resistance of the microcantilever was tracked on an Agilent 34970A data acquisition system with a sampling frequency of 1 Hz to 1/10 Hz. When the resistance changes of the cantilever were stabilized, the value was recorded and compared to a curve unique to that sensor derived from resistances produced in standard NaCl solutions of known osmolality (measured by a Fiske 110 freezing point depression osmometer) to determine the sample solution's osmolality.

C. Measuring Salivary Osmolality

Saliva samples obtained from volunteers were collected via expectoration into glass vials. Volunteers were instructed to refrain from eating or drinking for at least 30 minutes prior to providing a sample. The initial sample was pipetted into 0.5 mL aliquots in microcentrifuge tubes for measurement as described in Section A, above. No filtration, purification or centrifugation was preformed on the saliva samples prior to analysis. Saliva was collected unstimulated except for the act of expectoration and the psychological anticipation of providing a sample.

Example 1

Measurement of Osmolality of Untreated Saliva Samples as Compared to Standard Methods of Sample Preparation A. Measurement of Osmolality of Untreated Saliva Samples Initial attempts to obtain osmolality data from saliva using a hydrogel sensor was met with unstable osmolality readings and inconsistent results. Attempts to determine the osmolality of human saliva, led to sensor measurements which were slow, inaccurate, not reproducible, and elevated when compared to sensor measurements of saline solutions of similar osmolality (as determined by freezing point depression osmometry).

More specifically, when a hydrogel sensor was placed directly into an unprocessed saliva sample, the response of the sensor would take 15 minutes to over an hour to achieve a rate of change of cantilever resistance less than 0.1 Ohm/minute. Repeat measurements of identical saliva samples yielded inconsistent results, particularly if separated by different samples.

The cantilever resistance is correlated with the swelling state of the hydrogel. The imputed osmolality measurements were elevated. In other words, the swelling of the hydrogel in a saliva sample was significantly less than the swelling experienced by the hydrogel in a saline solution of the same osmolality as the saliva sample in question (FIG. 1).

B. Measurement of Osmolality of Saliva Samples Treated with Activated Carbon

Activated carbon treatment followed by filtration was evaluated as a possible way to remove interfering materials from saliva to improve the stability and accuracy of response of a hydrogel sensor in measurement of the osmolality of saliva samples. Saliva samples were treated by storage in a sealed vial with activated carbon for 15 minutes with 0.1 g/ml or 0.3 g/ml of activated carbon, followed by pipetting into microcentrifuge tubes for osmolality determination with a hydrogel sensor and by way of freezing point depression osmometry.

Figure 2:
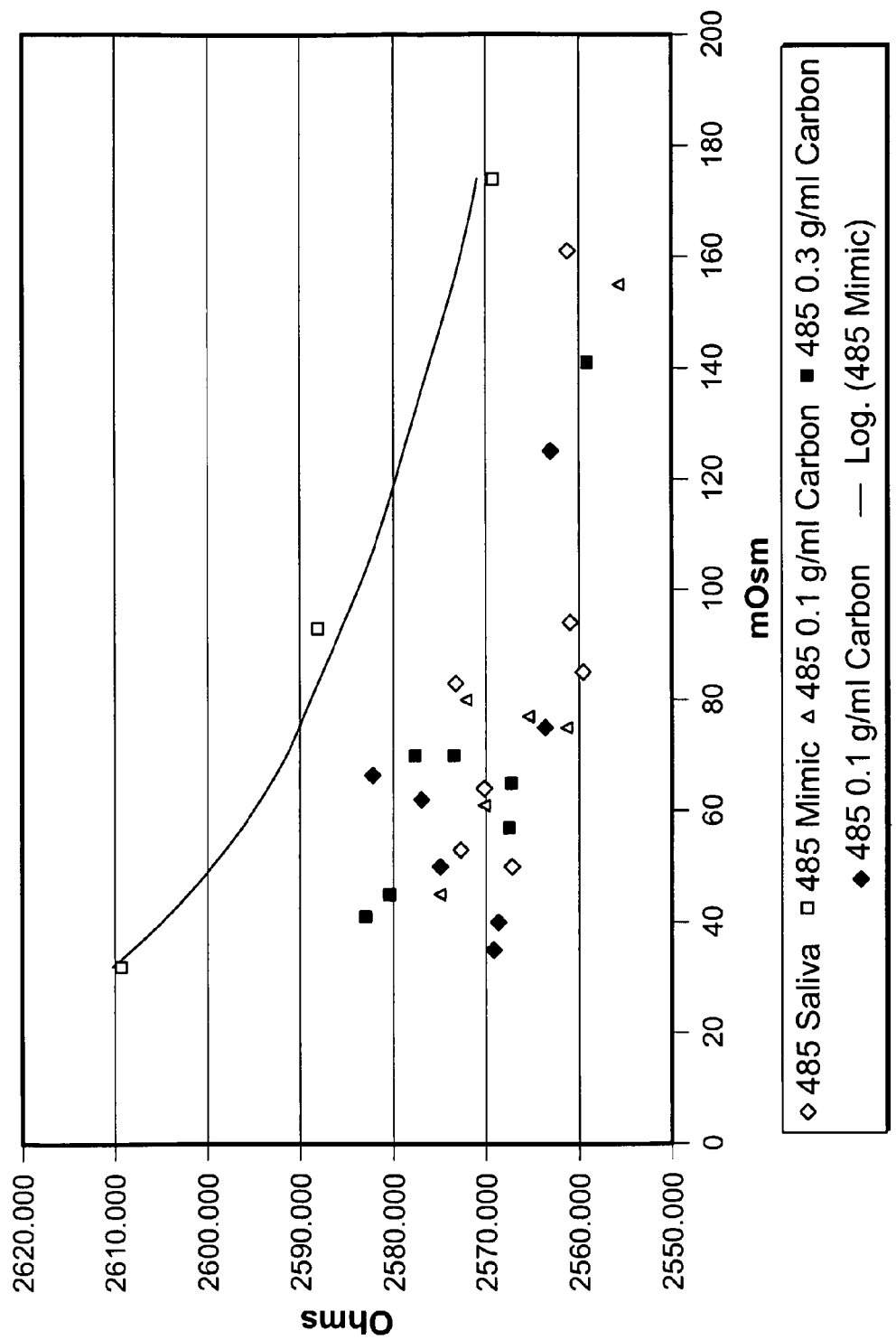
FIG. 2 is a graphic depiction of cantilever resistance (Ohms; sensor 485) versus solution osmolality (mOsm), for a human saliva sample (485 saliva); a reference NaCl solution (484 mimic), and saliva samples treated with activated carbon.

The results shown in FIG. 2 from sensor #485, indicate that activated carbon treatment did not improve the results when osmolality was evaluated using a hydrogel sensor. FIG. 2 is a graphic depiction of cantilever resistance (Ohms; sensor 485) versus solution osmolality (mOsm), for a human saliva sample (485 saliva); a reference NaCl solution (484 mimic), and saliva samples treated with: 0.1 g/ml activated carbon (485 0.1 g/ml Carbon); 0.3 g/ml activated carbon (485 0.3 g/ml Carbon); 0.1 g/ml activated carbon (485 0.1 g/ml Carbon).

Figure 3:
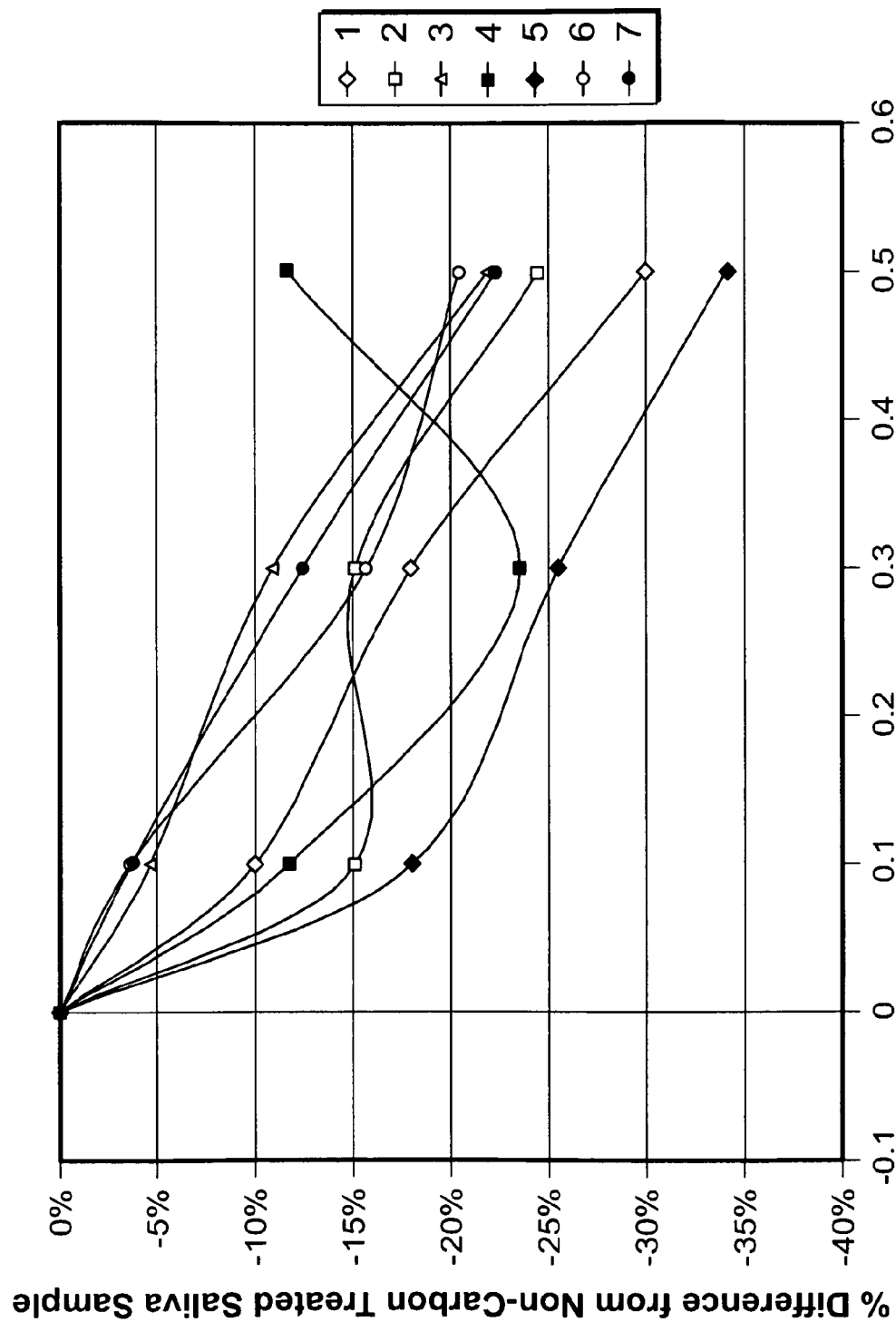
FIG. 3 is a graphic depiction of the effect of activated carbon treatment (0-0.6 g/ml) on individual saliva samples from seven volunteers.
Figure 4:
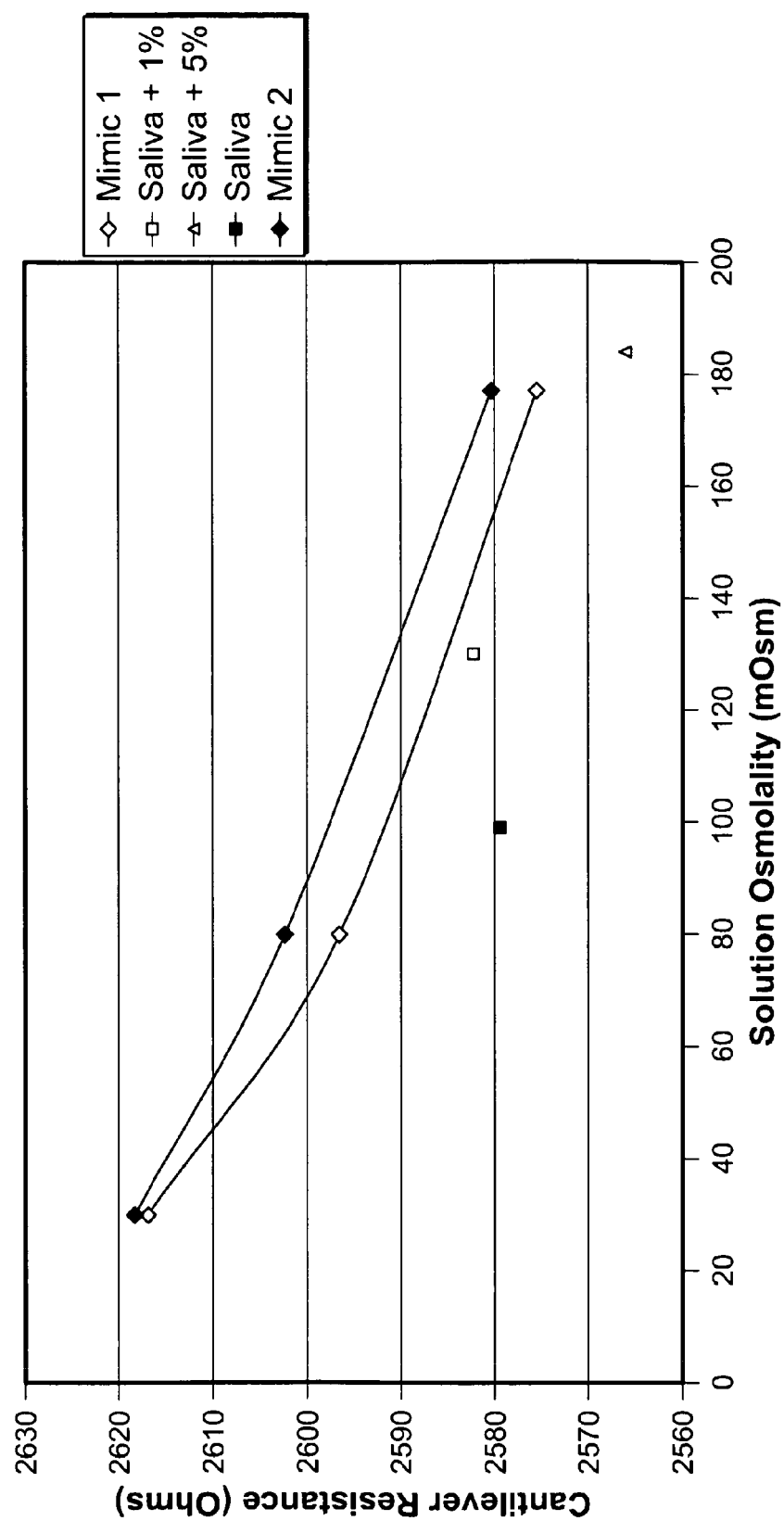
FIG. 4 is a graphic depiction of cantilever resistance (Ohms) versus solution osmolality (mOsm) for two NaCL solutions, untreated and Dowfax C10L-treated human saliva samples.
Figure 5:
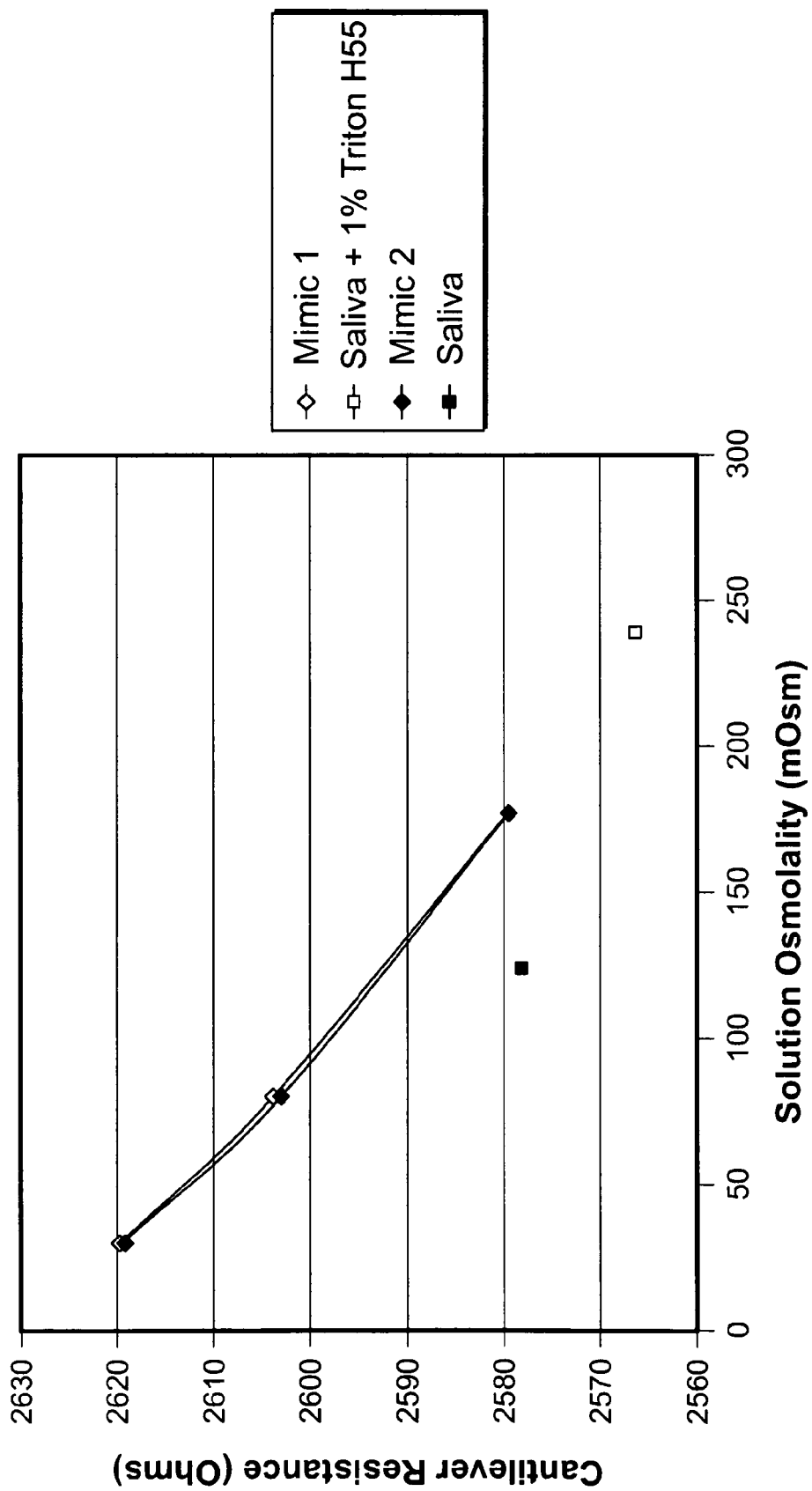
FIG. 5 is a graphic depiction of cantilever resistance (Ohms) versus solution osmolality (mOsm) for two NaCL solutions, untreated and a Triton H55-treated human saliva sample.
Figure 6:
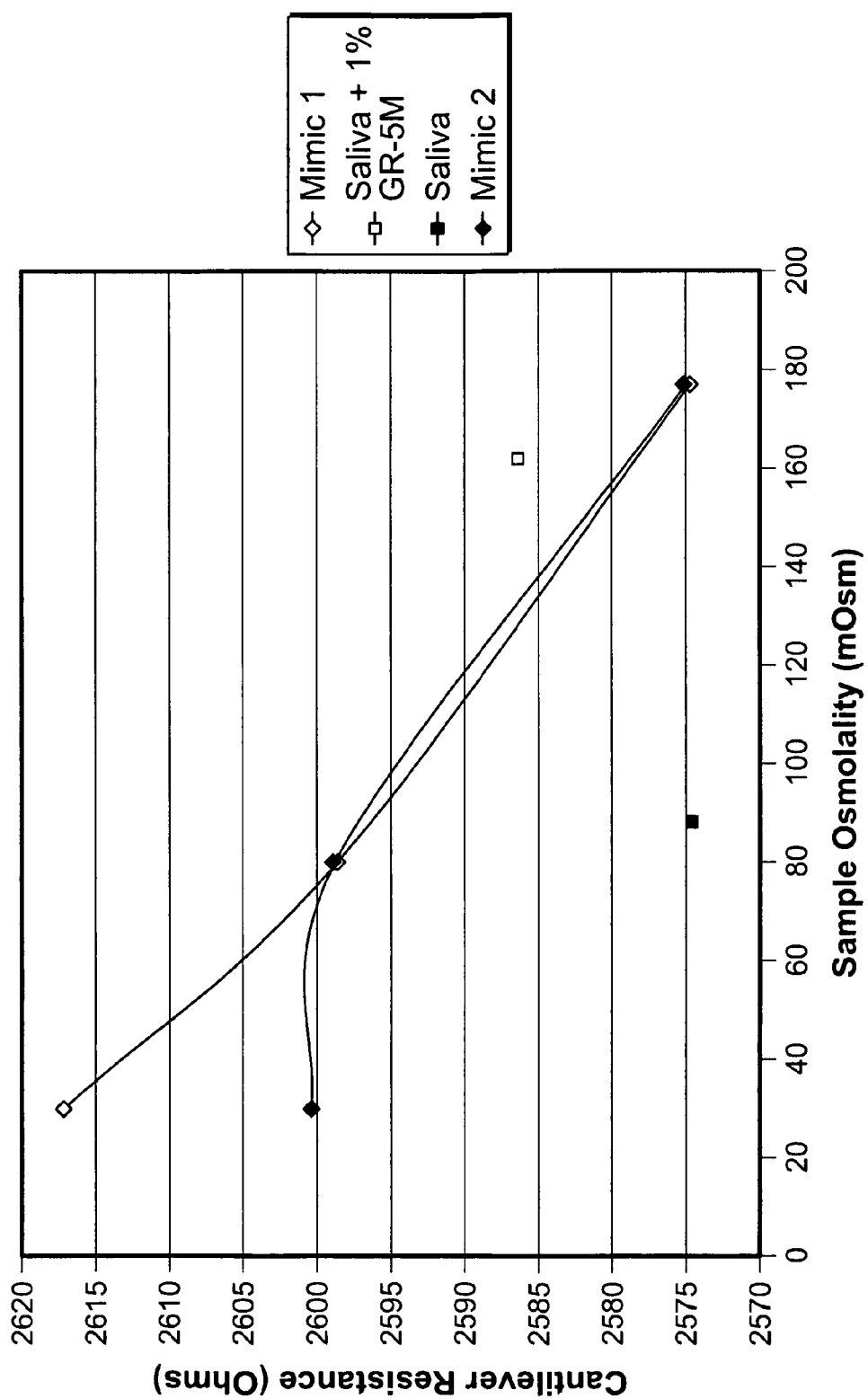
FIG. 6 is a graphic depiction of cantilever resistance (Ohms) versus solution osmolality (mOsm) for two NaCL solutions, untreated human saliva (saliva) and human saliva samples treated with 1% Triton GR-5M.

Following activated carbon treatment, the osmolality of the saliva sample decreased, as shown in FIG. 3, which shows the difference in osmolality between original and post-activated carbon-treated saliva samples from 7 volunteers. FIG. 3 provides a graphic depiction of the effect of activated carbon treatment (0-0.6 g/ml) on individual saliva samples from seven volunteers, reported as the percent (%) difference from non-carbon treated saliva samples. The reduction in osmolality for saliva from each of the 7 subjects indicates the carbon successfully adsorbed some solutes from saliva, but did not solve the problem of unstable osmolality readings and inconsistent The reduction in osmolality indicates the carbon successfully adsorbed some solutes from saliva, but did not solve the problem of unstable osmolality readings and inconsistent results, which were observed in untreated saliva samples.

C. Measurement of Osmolality of Model Samples Treated by Centrifugation

Using mucin as a model for an interfering saliva component, mucin containing saliva mimic solutions were prepared and processed using centrifuge filtration with 0.45 uM and 100 k MWCO (molecular weight cut-off) centrifuge filters. 100 k MWCO filtration was found to modestly improve the response of a hydrogel sensor in mucin solutions, but resulted in a poor yield and impractical handling requirements for a portable device.

D. Measurement of Osmolality of Saliva Samples Treated by Flocculent Addition

A generic "pool cleaner" type cationic flocculent was added to saliva samples in an attempt to precipitate larger biomolecules from the sample prior to measurement of osmolality using a hydrogel sensor. Flocculent was added at a concentration of 2 uL per 1 mL of saliva, and mixed. The samples were spun down in a microcentrifuge (Eppendorf 5415C at top speed) for 10 minutes. The supernatant was pipetted out and sampled using a hydrogel sensor and freezing point depression osmometry, as described above.

Example 2

Measurement of Osmolality of Saliva Samples Treated with Ion Exchange Resins

Further studies were carried out to determine if an accurate and consistent determination of saliva osmolality could be achieved by sample treatment with an ion exchange resin prior to measurement of osmolality using a hydrogel sensor.

It was eventually determined that treatment of saliva with certain ion exchange resins results in an accurate and consistent determination of saliva osmolality using hydrogel sensors consistent with results obtained using the freezing point depression method.

In carrying out the studies, sensing hydrogels were immersed in a dilute (0.05M) sodium hydroxide solution for one hour prior to use.

The results showed that treatment of saliva samples with various cation exchange or chelating resins at a final concentration of from about 0.001 meq exchange capacity/ml to about 0.05 meq exchange capacity/ml for a time period of from about 20 seconds to about 5 minutes or longer resulted in consistent and accurate values when saliva osmolality was measured using a hydrogel sensor.

A. Saliva Samples Treated with Ion Exchange Resin (IER)

Saliva samples were collected from individuals and 250 microliters of saliva was added to micro-centrifuge tubes.

Before and after IER treatment, the osmolality of the samples was measured on a Fiske 310 osmometer. All samples were then refrigerated overnight, and tested on sensors the following day.

Figure 7A:
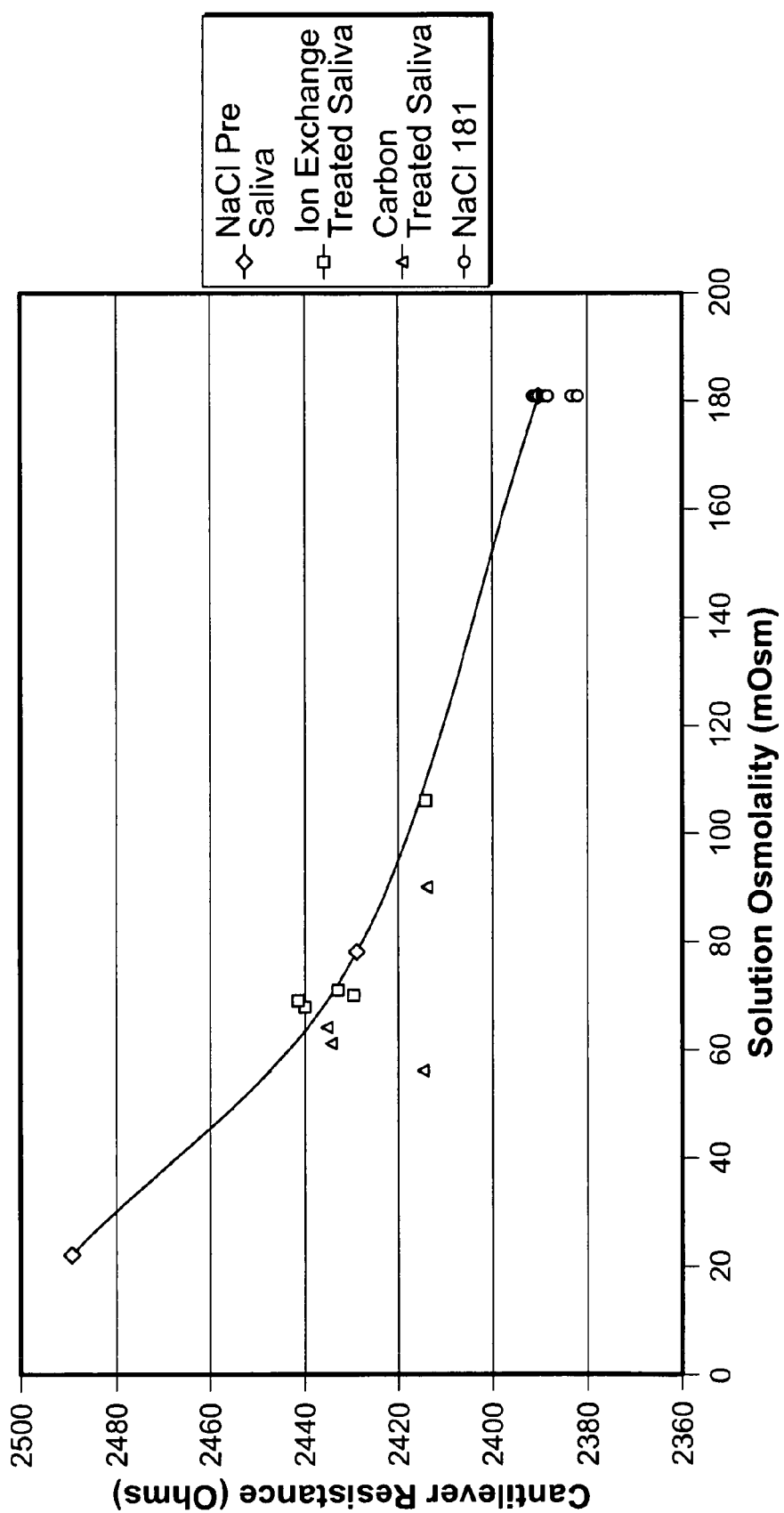
FIG. 7A is a graphic depiction of cantilever resistance (Ohms) versus solution osmolality (mOsm) for saliva treated with an ion exchange resin (Ion Exchange Treated Saliva) as compared to activated carbon-treated saliva (Carbon Treated Saliva) and a 181 mOsm NaCl solution (NaCl 181 mOsm).
Figure 7B:
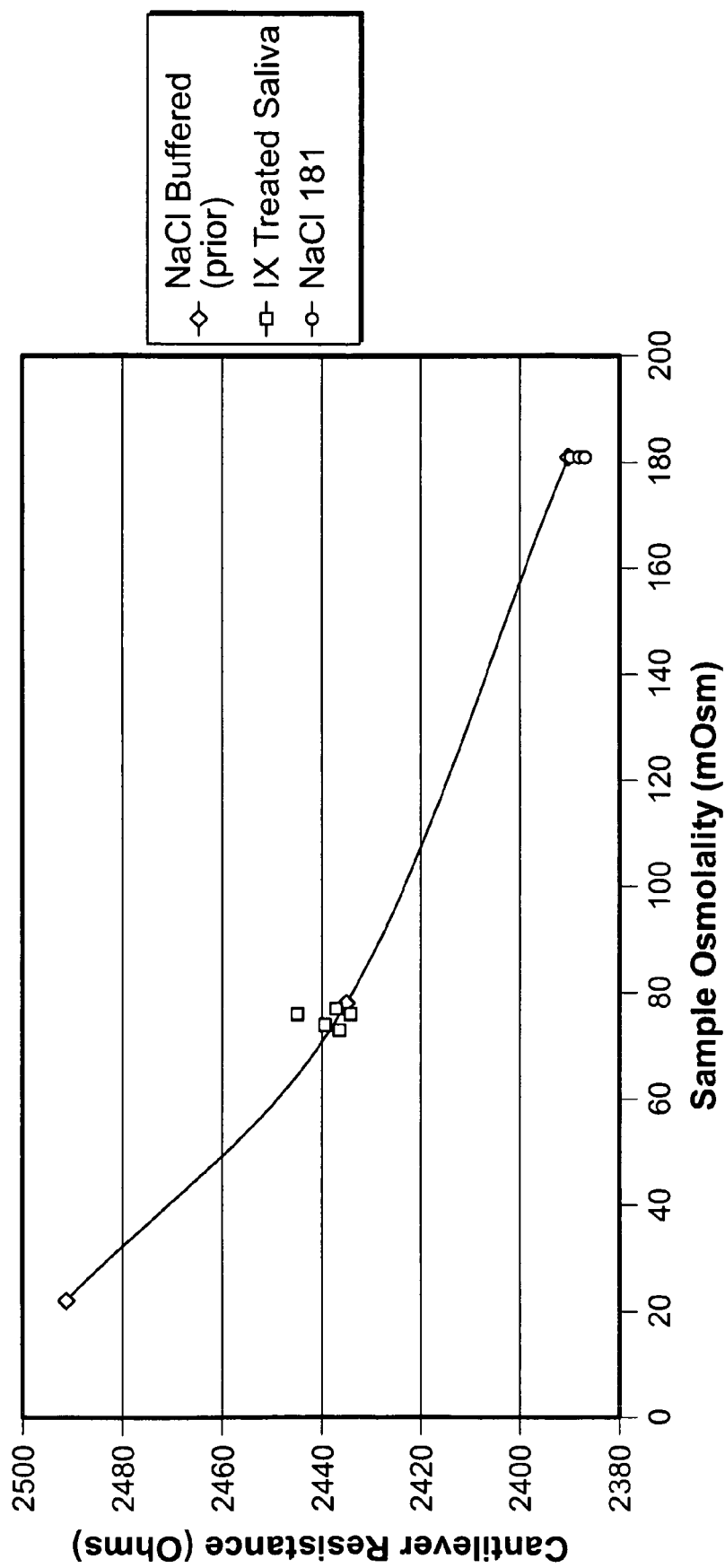
FIG. 7B is a graphic depiction of cantilever resistance (Ohms) versus sample osmolality (mOsm) for saliva treated 1× with an ion exchange resin (1× Treated saliva), as compared to NaCl solution adjusted a pH of 7 to 7.5 with phosphate buffer (NaCl buffered (prior)) and an NaCl control (NaCl 181).

Further studies were carried out to test the hypothesis that interfering cations, e.g., divalent calcium ions are a factor in the difficulty in obtaining accurate, reliable and reproducible results when analyzing a physical or chemical property of a biological fluid, such as saliva, using a hydrogel sensor. A number of calcium chelating agents were tested and shown to improve sensor response yielding results that approximates those obtained with reference saline (NaCl) solutions, barring interference with the hydrogel from the chelating agent. For example, adding acids that chelate calcium shifts the sample pH and interferes with hydrogel behavior unless the amount of acid is accurately tailored to the quantity of calcium in the sample In one study, activated carbon treatment (at 0-0.6 g/ml) was compared to Amberlite® 718 treatment of saliva samples from human volunteers. FIG. 7A is a graphic depiction of cantilever resistance (Ohms) versus solution osmolality (mOsm) for saliva treated with an ion exchange resin (Ion Exchange Treated Saliva) as compared to activated carbon-treated saliva (Carbon Treated Saliva) and a 181 mOsm NaCl solution (NaCl 181 mOsm). FIG. 7B is a graphic depiction of cantilever resistance (Ohms) versus sample osmolality (mOsm) for saliva treated 1× with an ion exchange resin (1× Treated saliva), as compared to buffered NaCl (NaCl buffered (prior)) and an NaCl control (NaCl 181). Buffered NaCl solutions comprise distilled water and sodium chloride with the addition of small quantities of weak acid and base (sodium hydrogen phosphate and sodium dihydrogen phosphate) in equilibrium such that the solution pH remains stable despite exposure to atmospheric $CO_2$, and variations in temperature.

In particular, ion exchange resins (IERs) that are known to bind divalent cations, such as calcium, proved to be very effective. In addition, use of IERs in sample preparation provides the advantage that a precise amount of resin was not required to yield accurate, reliable and reproducible results when analyzing the osmolality of a biological fluid, such as saliva using a hydrogel sensor. In other words, use of a moderate excess of IER did not alter the timing or magnitude of sensor response nor sample osmolality.

In further studies, saliva was exposed (treated) with an IER at a concentration of between 0.46 g/mL and 0.92 g/mL in a vial. The IER settled to the bottom of the tube, and the supernatant saliva osmolality was measured. Physical observation of the saliva samples soon after exposure to the IER indicated that the saliva's viscosity and "stringiness" were significantly reduced. These observations suggest that deaggregation of saliva significantly improved the accuracy and consistency of the hydrogel sensor response in a determination of osmolality of saliva samples.

Addition of 0.92 g/mL of IER to saliva yielded osmolality values determined with hydrogel sensors that matched hydrogel sensor values for simple NaCl solutions. The upper limit of an amount of ion exchange medium for effective ion removal is governed by changes in osmolality resulting from the resin either being too dry (and absorbing water, thus increasing osmolality) or by adding water and reducing osmolality. In general, water soluble ion exchange media will contribute to osmolality potentially introducing an error. Thus, ion exchange media that does not absorb water is unlikely to have an upper limit for the amount that can be added to a sample and yield a reliable and accurate osmolality result with a hydrogel sensor, with the exception of the physical ability to contact the sample. However, with water-absorbing resins, addition of large amounts of ion exchange media to a sample can introduce error.

Samples treated with 0.46 g/mL IER for both were run the first day in parallel on 3 sensors. Samples treated with 0.92 g/mL IER for both were refrigerated and run the following day in parallel on 3 sensors. The samples treated with 0.46 g/mL IER yielded good results, however, the 0.92 g/mL IER samples looked even better. In the worst case, IER treatment modified the original saliva osmolality reading by 5 mOsm. The saliva data points fit the expected variability surrounding reference measurements with buffered NaCl.

B. Saliva Samples Treated with Ion Exchange Resin or Citric Acid

In another study, saliva samples were collected from individuals and divided into 12 1 mL sub-samples in microcentrifuge tubes. Six of the samples were treated with Amberlite® 718 resin, and six of the samples were treated with citric acid. The Amberlite® 718 resin was added at a concentration of approximately 0.46 g/mL of saliva, and citric acid was added at a concentration of approximately 0.08 mg/mL of saliva. The quantity of citric acid was calculated to be sufficient to complex the $Ca^{2+}$ ions from the reported normal human range in saliva with slight excess. Citric acid forms an insoluble complex with calcium, calcium citrate, which will precipitate from aqueous solutions.

Before and after IER and citric acid treatments, the osmolality of the samples was measured on a Fiske 310 osmometer. 10 uL of 1603 mOsm $CaCl_2$ solution was added to three of six IER-treated saliva samples and three of six citric acid samples, resulting in a calcium concentration of 0.2 mg/mL (above the higher reported literature values for saliva calcium content). All samples were then refrigerated overnight, and tested on sensors the following day.

TABLE 1

Effect of the Concentration of Activated Carbon, Citric Acid and Various IERs on Saliva Osmolality Measurement

| Chelating Agent | Conc. | FPO (mOsm) | Sensor Measured (mOsm) | Difference |
|---|---|---|---|---|
| Citric Acid | 0.08 mg/mL | 70 | 110 | 40 |
| Amberlite 718 | 0.46 g/mL | 77 | 89 | 12 |
| Amberlite 718 | 0.16 g/mL | 85 | 90 | 5 |
| Amberlite 718 | 0.24 g/mL | 88 | 94 | 6 |
| Amberlite 748 | 0.24 g/mL | 86 | 88 | 2 |
| Amberlite 748 | 0.16 g/mL | 87 | 95 | 8 |
| Amberlite 748 | 0.24 g/mL | 86 | 92 | 6 |
| SACMP | 0.24 g/mL | 97 | 87 | −10 |
| SACMP | 0.16 g/mL | 81 | 95 | 14 |
| Amberlite 718 (Buffered NaCl) | 0.46 g/mL | 78 | 80 | 2 |
| Amberlite 718 (Buffered NaCl) | 0.16 g/mL | 78 | 81 | 3 |

A single sensor combining saliva treatment and measurement was prepared as follows. An osmotic sensor was constructed as detailed above and a 5 pt NaCl calibration was obtained.

Figure 11A:
FIGS. 11A and B are photomicrographs of sensors comprised of a piezoresistive microcantilever coupled to as osmotically responsive hydrogel with a fiber form cation exchange media bonded on the sensor, after dipping or scooping (FIG. 11A) or after drying in the oven at 70 C for 5 minutes (FIG. 11B).
Figure 11B:
Figure 12:
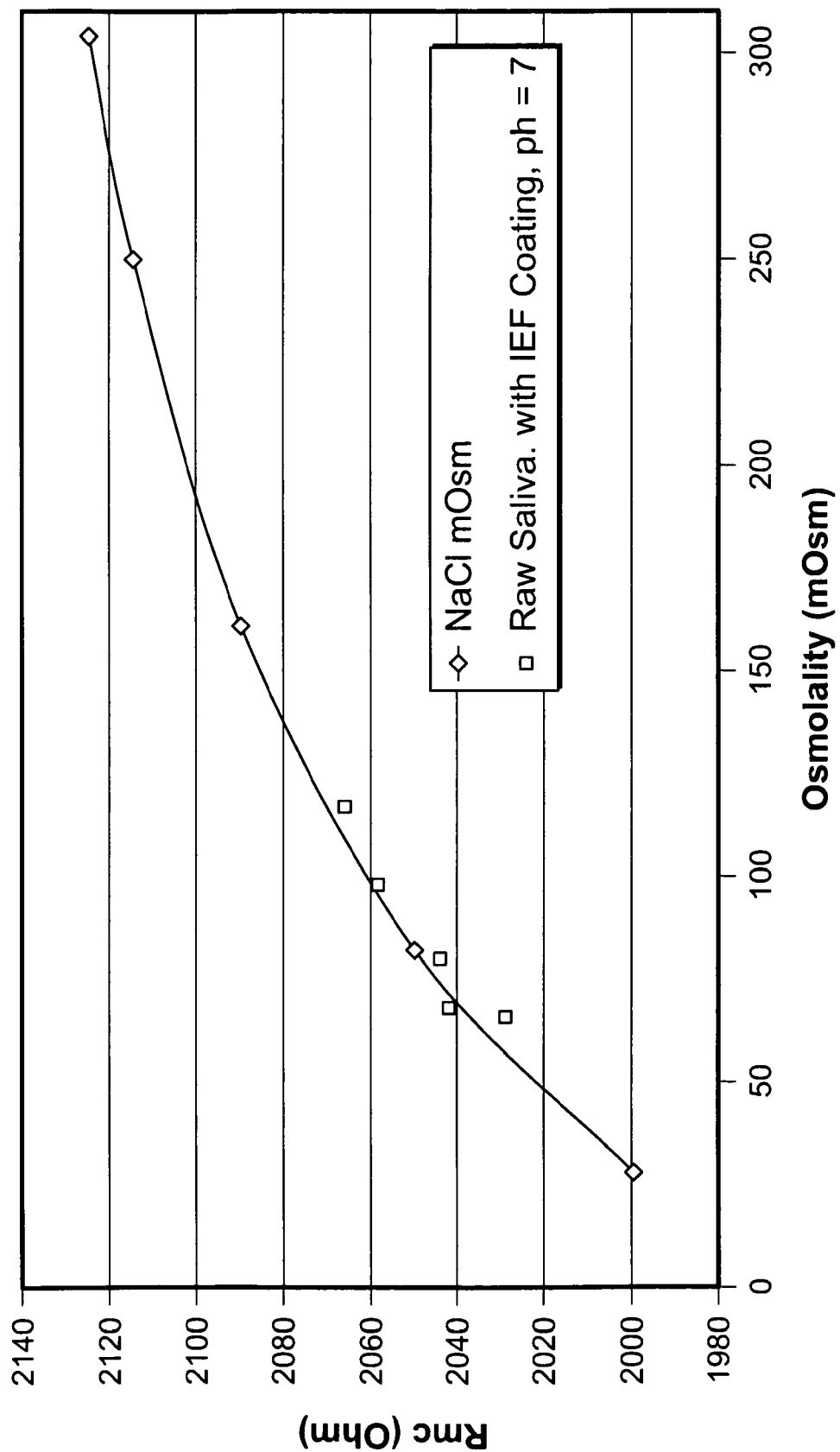
FIG. 12 a graphic depiction of cantilever resistance (Ohms) for sensor #2004 (BM42-178D), wherein the sensor was covered IEF powder (as shown in FIGS. 11A and B) and used to test the osmolality (mOsm) of a NaCl control versus saliva.

0.15 g Fibrous Cation Exchange material (Whatman P11 Cellulose Phosphate) was mixed in 1 ml DI water in a small vial. The pH was adjusted to using 0.1M NaOH. The sensor was then immersed in the ion exchange fiber solution and removed such that fibers covered the sensor area (FIG. 11A). Fiber coated sensor was then placed in a 70 C oven for five minutes. This sensor was then used to directly measure saliva Osmolality with acceptable accuracy. (FIG. 11B).

To confirm that removal of calcium was a significant factor in the improved salivary osmolality measurements using hydrogel sensors, a study was preformed where calcium was directly added to samples after IER or citric acid treatment, and osmolality was re-measured.

Figure 8A:
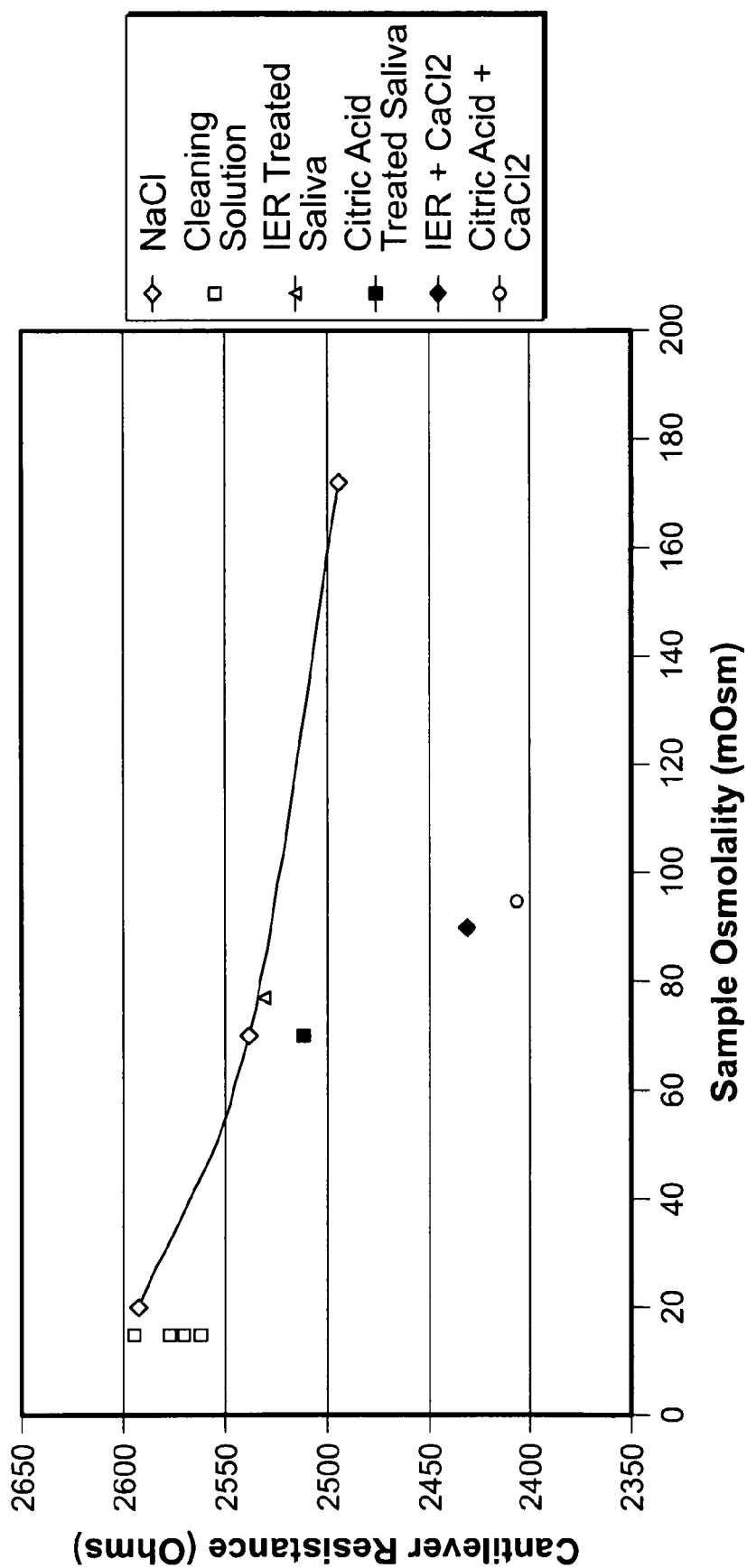
FIGS. 8A and B provide a graphic depiction of cantilever resistance (Ohms) versus sample osmolality (mOsm) for saliva treated with: an ion exchange resin (IER Treated Saliva), Citric Acid (Citric Acid Treated Saliva), an ion exchange resin and $CaCl_2$ (IER+$CaCl_2$), Citric Acid and $CaCl_2$ (Citric Acid+$CaCl_2$), as compared to an NaCl control (FIG. 8A, Sensor 1059.
Figure 8B:
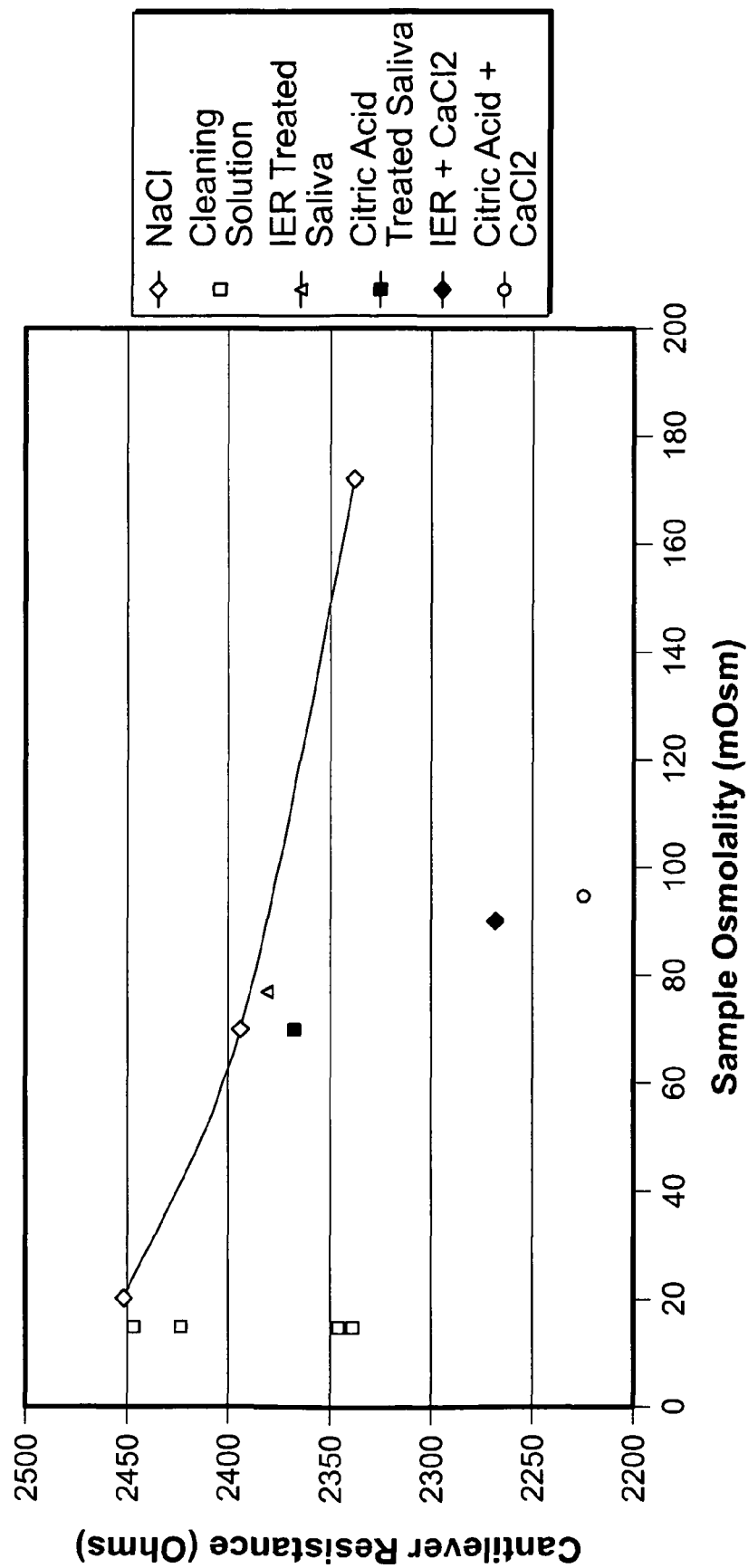
FIG. 8B, Sensor 1066.
Figure 9:
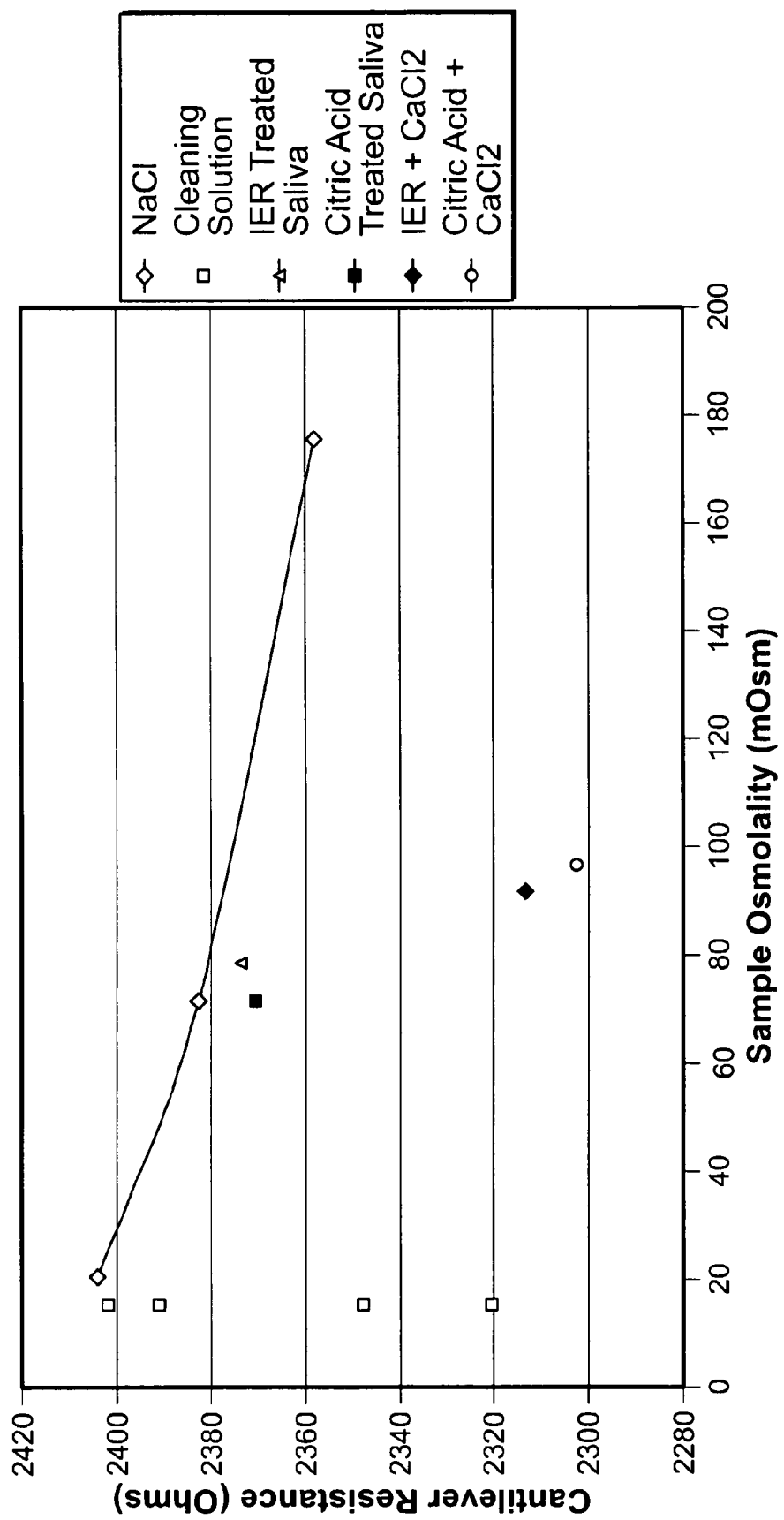
FIG. 9 is a graphic depiction of cantilever resistance (Ohms) versus sample osmolality (mOsm) for saliva treated with: an ion exchange resin (IER Treated Saliva), Citric Acid (Citric Acid Treated Saliva), an ion exchange resin and $CaCl_2$ (IER+$CaCl_2$), and Citric Acid and $CaCl_2$ (Citric Acid+$CaCl_2$), as compared to a NaCl control (Sensor 1073).

FIGS. 8A and B provide a graphic depiction of cantilever resistance (Ohms) versus sample osmolality (mOsm) for saliva treated with: an ion exchange resin (IER Treated Saliva), Citric Acid (Citric Acid Treated Saliva), an ion exchange resin and $CaCl_2$ (IER+$CaCl_2$), Citric Acid and $CaCl_2$ (Citric Acid+$CaCl_2$), as compared to an NaCl control (FIG. 8A, Sensor 1059; FIG. 8B, Sensor 1066). FIG. 9 is a graphic depiction of cantilever resistance (Ohms) versus sample osmolality (mOsm) for saliva treated with: an ion exchange resin (IER Treated Saliva), Citric Acid (Citric Acid Treated Saliva), an ion exchange resin and $CaCl_2$ (IER+$CaCl_2$), and Citric Acid and $CaCl_2$ (Citric Acid+$CaCl_2$), as compared to an NaCl control (Sensor 1073).

The results show that IER treatment of saliva samples resulted in an accurate determination of saliva osmolality using a hydrogel sensor. Citric acid treatment improved sensor response via calcium removal, but altered solution osmolality such that it was not effective at yielding an accurate overall result with the hydrogel sensors. In addition, when $CaCl_2$ was added to IER treated saliva, an inaccurate result was obtained suggesting that the IER is removing calcium and that calcium interferes with the accurate determination of saliva osmolality using a hydrogel sensor.

Figure 10:
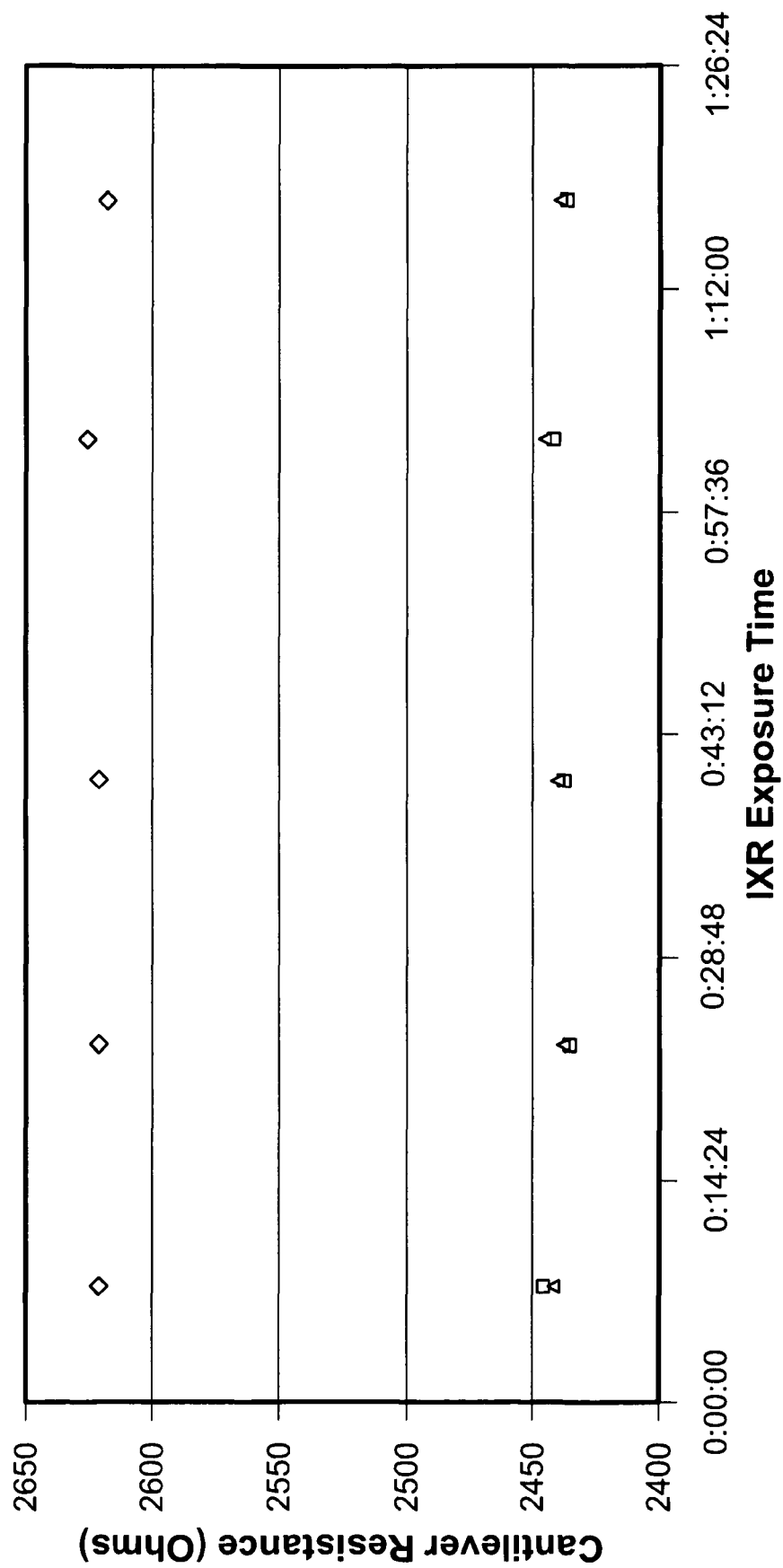
FIG. 10 a graphic depiction of cantilever resistance (Ohms) versus IER exposure time for 3 different sensors for a time period up to about 1.5 hours.

In a further study, the stability of hydrogel sensor response in measurement of osmolality of saliva samples treated with IERs was evaluated. FIG. 10 is a graphic depiction of cantilever resistance (Ohms) versus IER exposure time for 3 different sensors for a time period up to about 1.5 hours. The results show that the cantilever resistance (Ohms) and therefore the osmolality measurement was stable for all 3 sensors for a time period of at least 1.5 hours.

Example 3

Measurement of Osmolality of Tear and Blood or Serum Samples

Tear film is readily obtained by the capillary collection method and can be treated with an ion exchange resin prior to analysis and then spotted onto the microcantilever sensor. A convenient tear film osmometer was constructed by coating microfiber cation exchange resin onto a microcantilever sensor. The sensor is then directly placed on the outer surface of the cornea to measure tear film properties including osmolality.

The osmolality of whole blood and serum are commonly measured using a freezing point or vapor pressure osmometer. Whole blood (100 uL) was obtained using a finger stick lanced and spotted directly onto a sensor prepared as described hereinabove and coated with IEF powder (as shown in FIGS. 11A and B). The sensor reached an equilibrium resistance value within 3 minutes corresponding to 308 mOsmol.

Although the foregoing invention has been described in some detail by way of illustration and example for purposes of clarity and understanding, it will be apparent to those skilled in the art that certain changes and modifications may be practiced. Various aspects of the invention have been achieved by a series of experiments, some of which are described by way of the following non-limiting examples. Therefore, the description and examples should not be construed as limiting the scope of the invention, which is delineated by the appended description of exemplary embodiments.

What is claimed is:

1. A method for measuring a physical or chemical property of a biological fluid collected from a subject comprising substances which interfere with a physical or chemical property of a hydrogel, comprising
   a. treating a biological fluid sample with an ion exchange material;
   b. contacting the ion exchange material-treated biological fluid sample with a sensor comprising a hydrogel responsive by a change in a physical or chemical property to the biological fluid sample;
   by said treating, minimizing the effect of the interfering substances on the hydrogel when said ion exchange material-treated biological fluid sample is contacted with the sensor;
   c. evaluating a change in said physical or chemical property of said hydrogel in response to contact with said ion exchange material-treated biological fluid sample; and
   d. correlating the change in said hydrogel sensor with a physical or chemical property of said biological fluid sample.

2. The method according to claim 1, wherein said biological fluid is selected from the group consisting of saliva, whole blood, plasma, serum, tear fluid, lymph, synovial fluid, urine, sputum, semen, vaginal lavage, bone marrow and cerebrospinal cord fluid.

3. The method according to claim 2, wherein said biological fluid is saliva.

4. The method according to claim 1, wherein the change in said physical or chemical property of said hydrogel is a change in volume, a change in optical density, a change in refractive index or a change in AC conductivity.

5. The method according to claim 1, wherein said hydrogel is a cross-linked hydrogel having a net negative charge.

6. The method according to claim 5, wherein said hydrogel is a cross-linked hydrogel comprised of a hydroxyalkyl acrylate, a hydroxyalkyl methacrylate, a vinyl ether, or a vinyl pyrrolidone.

7. The method according to claim 1, wherein said hydrogel comprises an anionic moiety selected from a carboxylate group, a sulfate group, a sulfonate group and a phosphate group.

8. The method according to claim 1, wherein said ion exchange material is a cation exchange resin.

9. The method according to claim 1, wherein said ion exchange material is a chelating resin.

10. The method according to claim 9, wherein said chelating resin comprises an iminodiacetic acid functionality.

11. The method according to claim 1, wherein said ion exchange material is selected from the group consisting of a water insoluble polymeric cation exchange resin, EDTA, oxalic acid, citric acid and a water soluble polyacrylate.

12. The method according to claim 1, wherein said treatment is effective to remove $Ca^{2+}$ from the biological fluid sample.

13. The method according to claim 1, wherein the physical or chemical property of said biological fluid sample is a physical property selected from the group consisting of absorption at a given wavelength, density, electric conductivity, pH, osmolality, osmolarity, thermal transfer, viscosity, dielectric constant, refractive index and light scattering.

14. The method according to claim 13, wherein said physical property is osmolality.

15. The method according to claim 1, wherein said physical or chemical property of said biological fluid sample is a chemical property selected from the group consisting of the concentration of glucose, creatinine, urea, cortisol, total protein, total electrolytes, estrogen, progesterone, testosterone, a cation, and an anion.

16. The method according to claim 15, wherein said cation is selected from the group consisting of sodium ($Na^+$); calcium ($Ca^{2+}$); potassium ($K^+$),and magnesium ($Mg^{2+}$).

17. The method according to claim 15, wherein said anion is selected from the group consisting of chloride ($Cl^-$), fluoride (Fl), bromide (Br), sulfate ($SO_4^{2-}$), nitrate ($NO_3^-$), carbonate ($CO_3^{2-}$),and bicarbonate ($HCO_3^-$).

18. The method according to claim 1, wherein said evaluating comprises monitoring said hydrogel for a decrease in volume to detect a saliva osmolality.

19. The method according to claim 1, wherein said evaluating comprises monitoring the hydrogel for an increase in hydrogel volume to detect saliva osmolality.

20. A method for measuring osmolality of a saliva biological sample, comprising:
   treating the saliva biological fluid sample with an ion exchange resin;
   contacting the ion exchange resin-treated saliva biological fluid sample with a sensor comprising a hydrogel responsive by a change in volume to the treated saliva biological fluid sample;
   evaluating a change in volume of said hydrogel in response to contact with said ion exchange resin-treated saliva biological fluid sample; and
   correlating the change in said sensor with the osmolality of said saliva biological fluid sample.

* * * * *